US012760062B2

(12) United States Patent
Narayan et al.

(10) Patent No.: US 12,760,062 B2
(45) Date of Patent: Oct. 13, 2026

(54) PROCESS OF STORING AND PREPARING THE PROTEIN

(71) Applicant: Kashiv BioSciences, LLC, Piscataway, NJ (US)

(72) Inventors: Om Narayan, Ahmedabad (IN); Tarun Kumar Gupta, Ahmedabad (IN); Mayankkumar Thakkar, Ahmedabad (IN); Kishor Galani, Surat (IN)

(73) Assignee: Kashiv BioSciences, LLC, Piscataway, NJ (US)

( * ) Notice: Subject to any disclaimer, the term of this patent is extended or adjusted under 35 U.S.C. 154(b) by 841 days.

(21) Appl. No.: 17/928,101

(22) PCT Filed: May 28, 2021

(86) PCT No.: PCT/IB2021/054693
§ 371 (c)(1),
(2) Date: Nov. 28, 2022

(87) PCT Pub. No.: WO2021/240458
PCT Pub. Date: Dec. 2, 2021

(65) Prior Publication Data

US 2023/0348530 A1 Nov. 2, 2023

(30) Foreign Application Priority Data

May 28, 2020 (IN) ............................ 202021022374

(51) Int. Cl.
*C07K 1/16* (2006.01)
*A61K 47/18* (2017.01)
*A61K 47/34* (2017.01)
*A61K 47/36* (2006.01)
*A61K 47/54* (2017.01)
*C07K 16/42* (2006.01)

(52) U.S. Cl.
CPC ............ *C07K 1/165* (2013.01); *A61K 47/183* (2013.01); *A61K 47/34* (2013.01); *A61K 47/36* (2013.01); *A61K 47/548* (2017.08); *C07K 16/4291* (2013.01)

(58) Field of Classification Search
CPC .............. C07K 1/165; C07K 16/41219; A61K 47/548; A61K 47/183; A61K 47/34
See application file for complete search history.

(56) References Cited

U.S. PATENT DOCUMENTS

| | | | |
|---|---|---|---|
| 5,328,834 | A | 7/1994 | Ngo et al. |
| 8,703,126 | B2 | 4/2014 | Liu et al. |
| 9,291,630 | B1 | 3/2016 | Wezeman et al. |
| 9,352,035 | B2 | 5/2016 | Zhou et al. |
| 9,382,317 | B2 | 7/2016 | Manning et al. |
| 9,556,258 | B2 | 1/2017 | Nti-Gyabaah et al. |
| 9,598,718 | B2 | 3/2017 | Rupprechter et al. |
| 9,683,012 | B2 | 6/2017 | Yoon et al. |
| 10,034,940 | B2 | 7/2018 | Liu et al. |
| 10,080,793 | B2 | 9/2018 | Oever et al. |
| 10,618,960 | B2 | 4/2020 | Liu et al. |
| 12,139,510 | B2 | 11/2024 | Narayan et al. |
| 2006/0228780 | A1 | 10/2006 | Luo et al. |
| 2008/0064861 | A1 | 3/2008 | Sun |
| 2008/0167450 | A1 | 7/2008 | Pan |
| 2009/0252749 | A1 | 10/2009 | Leister et al. |
| 2010/0129379 | A1 | 5/2010 | Carpenter et al. |
| 2010/0278929 | A1 | 11/2010 | Wei et al. |
| 2011/0129468 | A1 | 6/2011 | Mccue et al. |
| 2012/0172299 | A1 | 7/2012 | Schmalz et al. |
| 2012/0322733 | A1 | 12/2012 | Shaw |
| 2013/0079498 | A1 | 3/2013 | Gilljam et al. |
| 2013/0197198 | A1 | 8/2013 | Sun et al. |
| 2013/0338344 | A1 | 12/2013 | Ramasubramanyan et al. |
| 2014/0288272 | A1 | 9/2014 | Allison et al. |
| 2014/0341843 | A1 | 11/2014 | Barnes et al. |
| 2015/0284673 | A1 | 10/2015 | Langer et al. |
| 2016/0115193 | A1 | 4/2016 | Herigstad et al. |
| 2016/0122384 | A1 | 5/2016 | Kim et al. |
| 2016/0228371 | A1 | 8/2016 | Schultz et al. |
| 2017/0007712 | A1 | 1/2017 | DeFrees et al. |
| 2017/0058019 | A1 | 3/2017 | Felföldi et al. |
| 2017/0305999 | A1 | 10/2017 | Leber et al. |
| 2017/0326069 | A1 | 11/2017 | Brunner-Schwarz et al. |
| 2018/0037642 | A1 | 2/2018 | Arakawa et al. |

(Continued)

FOREIGN PATENT DOCUMENTS

| | | | |
|---|---|---|---|
| CA | 2528906 | C | 7/2013 |
| CA | 3072129 | A1 | 3/2019 |

(Continued)

OTHER PUBLICATIONS

Pennington et al., "Structural basis of omalizumab therapy and omalizumab-mediated IgE exchange." Nature Communications. 7: 11610, p. 1-12. (Year: 2016).*
U.S. Appl. No. 17/922,729 20230167153, filed Nov. 1, 2022.
U.S. Appl. No. 18/416,846 20240158437, filed Jan. 18, 2024.
U.S. Appl. No. 18/416,844 20240239838, filed Jan. 18, 2024, U.S. Pat. No. 12,139,510, Nov. 12, 2024.
U.S. Appl. No. 18/893,058 20250011395, filed Sep. 23, 2024.
U.S. Appl. No. 19/092,641, filed Mar. 27, 2025.

(Continued)

*Primary Examiner* — Suzanne M Noakes
*Assistant Examiner* — Ciara A McKnight
(74) *Attorney, Agent, or Firm* — Goodwin Procter LLP

(57) ABSTRACT

The present invention provides a method for reducing the protein aggregation by adjusting the pH below 6.0 of liquid formulation comprising the antibody or fusion protein. The present invention also provides methods for storing the pre-formulation for longer period without using any sugar or additives which can be utilized for preparation of liquid or lyophilized formulation.

22 Claims, 1 Drawing Sheet

(56) References Cited

U.S. PATENT DOCUMENTS

| | | | |
|---|---|---|---|
| 2018/0208639 A1 | 7/2018 | Minter et al. | |
| 2018/0327446 A1 | 11/2018 | Fong et al. | |
| 2018/0333493 A1 | 11/2018 | Shenoy | |
| 2018/0344630 A1 | 12/2018 | Igawa et al. | |
| 2019/0062419 A1 | 2/2019 | Ramasubramanyan et al. | |
| 2019/0256556 A1 | 8/2019 | Giese et al. | |
| 2019/0298801 A1 | 10/2019 | Kerwin et al. | |
| 2019/0343918 A1 | 11/2019 | Graham et al. | |
| 2019/0353661 A1 | 11/2019 | Smith | |
| 2019/0358323 A1 | 11/2019 | Liu et al. | |
| 2020/0003714 A1 | 1/2020 | Gillespie et al. | |
| 2020/0017569 A9 | 1/2020 | Leister et al. | |
| 2020/0088749 A1 | 3/2020 | Salbato et al. | |
| 2020/0230242 A1 | 7/2020 | Desai et al. | |
| 2020/0283472 A1 | 9/2020 | Karur | |
| 2021/0079422 A1 | 3/2021 | Oh et al. | |
| 2021/0122782 A1 | 4/2021 | Eisenhuth et al. | |
| 2021/0130396 A1 | 5/2021 | Sutter et al. | |
| 2021/0179690 A1 | 6/2021 | Jayaraman et al. | |
| 2021/0230250 A1 | 7/2021 | Lazar et al. | |
| 2022/0194980 A1 | 6/2022 | Leiss et al. | |
| 2022/0203347 A1 | 6/2022 | Wong et al. | |
| 2022/0260521 A1 | 8/2022 | Upadhyay | |
| 2022/0267473 A1 | 8/2022 | Weaver et al. | |
| 2023/0124565 A1 | 4/2023 | Yang et al. | |
| 2023/0166200 A1 | 6/2023 | Narayan et al. | |
| 2023/0166201 A1 | 6/2023 | Narayan et al. | |
| 2023/0167153 A1 | 6/2023 | Narayan et al. | |
| 2023/0303621 A1 | 9/2023 | Mahajan | |
| 2023/0340080 A1 | 10/2023 | Sharma et al. | |
| 2023/0348530 A1 | 11/2023 | Narayan et al. | |
| 2024/0077483 A1 | 3/2024 | Kuppili et al. | |
| 2024/0156907 A1 | 5/2024 | Narayan et al. | |
| 2024/0158437 A1 | 5/2024 | Narayan et al. | |
| 2024/0254160 A1 | 8/2024 | Upadhyay et al. | |
| 2024/0287159 A1 | 8/2024 | Sharma et al. | |
| 2024/0317799 A1 | 9/2024 | Narayan et al. | |
| 2024/0343758 A1 | 10/2024 | Narayan et al. | |
| 2024/0343776 A1 | 10/2024 | Narayan et al. | |
| 2024/0400612 A1 | 12/2024 | Narayan et al. | |
| 2025/0011395 A1 | 1/2025 | Narayan et al. | |
| 2025/0043027 A1 | 2/2025 | Weaver et al. | |
| 2025/0059230 A1 | 2/2025 | Upadhyay et al. | |

FOREIGN PATENT DOCUMENTS

| | | | | |
|---|---|---|---|---|
| CN | 103405756 A | 11/2013 | | |
| CN | 103667225 A | 3/2014 | | |
| CN | 106190935 A | 12/2016 | | |
| CN | 109142728 A | 1/2019 | | |
| WO | WO-1998/001549 A2 | 1/1998 | | |
| WO | WO-2002/082066 A1 | 10/2002 | | |
| WO | WO-2005/044856 A2 | 5/2005 | | |
| WO | WO-2009/058769 A1 | 5/2009 | | |
| WO | WO-2010/102241 A1 | 9/2010 | | |
| WO | WO-2011150110 A1 * | 12/2011 | ............ | C07K 1/165 |
| WO | WO-2012/160032 A1 | 11/2012 | | |
| WO | WO-2013/071396 A1 | 5/2013 | | |
| WO | WO-2013/096791 A1 | 6/2013 | | |
| WO | WO-2013/180647 A1 | 12/2013 | | |
| WO | WO-2015/189832 A1 | 12/2015 | | |
| WO | WO-2016/009049 A1 | 1/2016 | | |
| WO | WO-2017/180594 A1 | 10/2017 | | |
| WO | WO-2019/043067 A1 | 3/2019 | | |
| WO | WO-2019/224842 A1 | 11/2019 | | |
| WO | WO-2019/224843 A1 | 11/2019 | | |
| WO | WO-2021/009669 A2 | 1/2021 | | |
| WO | WO-2021/038532 A1 | 3/2021 | | |
| WO | WO-2021/181417 A1 | 9/2021 | | |
| WO | WO-2021/220251 A1 | 11/2021 | | |
| WO | WO-2021/220252 A1 | 11/2021 | | |
| WO | WO-2021/220253 A1 | 11/2021 | | |
| WO | WO-2021/240458 A2 | 12/2021 | | |
| WO | WO-2022/195505 A1 | 9/2022 | | |
| WO | WO-2022/201056 A1 | 9/2022 | | |
| WO | WO-2023/047368 A1 | 3/2023 | | |
| WO | WO-2023/053030 A1 | 4/2023 | | |
| WO | WO-2023/053031 A1 | 4/2023 | | |
| WO | WO-2023/053032 A1 | 4/2023 | | |
| WO | WO-2023/057994 A1 | 4/2023 | | |
| WO | WO-2023/057995 A1 | 4/2023 | | |
| WO | WO-2023/112000 A2 | 6/2023 | | |
| WO | WO-2023/180977 A1 | 9/2023 | | |

OTHER PUBLICATIONS

U.S. Appl. No. 17/922,734 20230166200, filed Nov. 1, 2022.
U.S. Appl. No. 17/922,742 20230166201, filed Nov. 1, 2022.
U.S. Appl. No. 18/972,007 20250099873, filed Dec. 6, 2024.
U.S. Appl. No. 17/627,477 2022-0260521, filed Jan. 14, 2022.
U.S. Appl. No. 17/682,314 2022-0267473, filed Feb. 28, 2022.
U.S. Appl. No. 18/926,965 20250043027, filed Oct. 25, 2024.
U.S. Appl. No. 17/934,950 20230340080, filed Sep. 23, 2022.
U.S. Appl. No. 18/657,920 2024-0287159, filed May 8, 2024.
U.S. Appl. No. 18/125,616 20230303621, filed Mar. 23, 2023.
U.S. Appl. No. 18/262,316 20240077483, filed Jul. 20, 2023.
U.S. Appl. No. 18/550,920 20240156907, filed Sep. 15, 2023.
U.S. Appl. No. 18/620,649 2024-0343758, filed Mar. 28, 2024.
U.S. Appl. No. 18/620,441 2024-0317799, filed Mar. 28, 2024.
U.S. Appl. No. 18/620,255 2024-0343776, Mar. 28, 2024.
U.S. Appl. No. 18/696,701 20240400612, filed Mar. 28, 2024.
U.S. Appl. No. 18/699,511, filed Apr. 8, 2024.
U.S. Appl. No. 18/629,465 2024-0254160, filed Apr. 8, 2024.
U.S. Appl. No. 18/720,877 20250059230, filed Jun. 17, 2024.
Aasim et al., "The role of ligands on protein retention in adsorption chromatography: A surface energetics approach", p. 618-624, Journal of Separation Science, vol. 37, Issue 6. Jan. 21, 2014.
Ahmed et al. (1992) "Biosep-SEC-S high-performance size-exclusion chromatographic columns for proteins and peptides," Journal of Chromatography 599:25-33.
Balbino et al., "The anti-IgE mAb omalizumab induces adverse reactions by engaging Fc receptors", J. Clin. Invest., 2020, 130(3):1330-1335.
Center for Drug Evaluation and Research et al., Product Quality Reviews 2024, FDA, pp. 1-161, https://www.accessdata.fda.gov/drugsatfda_docs/nda/2018/761075Orig 1 s000Chem R. pdf (Year: 2024).
Cohen et al., "Switching Reference Medicines to Biosimilars: A Systematic Literature Review of Clinical Outcomes", Drugs, Mar. 3, 2018, vol. 78, Iss. 4, pp. 463-478. (16 pages).
Friess et al., "Microarray-based identification of differentially expressed growth- and metastasis-associated genes in pancreatic cancer", Cellular and Molecular Life Sciences, vol. 60, Jun. 2003, pp. 1180-1199.
GE Healthcare Life Sciences (2013) Multi modal Chromatography Handbook. GE Healthcare Bio-Sciences AB, Bjorkgatan 30, 751 84 Uppsala, Sweden, 2013, pp. 1-113.
Geng et al., "Inhibition of autoregulated TGFbeta signaling simultaneously enhances proliferation and differentiation of kidney epithelium and promotes repair following renal ischemia", Am. J. Pathol., Dec. 16, 2010, vol. 174, No. 4, pp. 1291-1308.
Goke, et al. (1988) "Identification of Rat Pancreatic Secretory Proteins after Separation by High-Performance Liquid Chromatography," Pancreas 3(2):199-206.
Gu et al. (2019) "Assessment of CE-based baseline disturbances using simulation and targeted experimental evaluation-impact on the purity determination of therapeutic proteins," Analytical and Bioanalytical Chemistry 411:2425-2437.
Guo et al. (2019) "Exploring metabolic biomarkers and regulation pathways of acute pancreatitis using ultra-performance liquid chromatography combined with a mass spectrometry-based metabolomics strategy," RSC Adv 9:12162-12173.
Guttman et al. (2020) "Better Separation Resolution of New Biopharmaceutical Modalities through Fine Tuning of the Temperature with CE-SOS" SCIEX, pp. 1-5.
Herniman et al., "Development of ultrahigh-performance liquid chromatography/mass spectrometry and ultrahigh-performance supercritical fluid chromatography/mass spectrometry assays to determine the concentration of BitrexTM and sodium saccharin in

(56) References Cited

OTHER PUBLICATIONS homemade facemask fit testing solutions", Rapid Communications in Mass Spectrometry, vol. 34, Iss. 16, Jun. 3, 2020, pp. 1-6.
International Search Report and Written Opinion for PCT/IB2020/056593 mailed Feb. 8, 2021 (10 pages).
International Search Report and Written Opinion for PCT/IB2020/058080 mailed Feb. 8, 2021 (12 pages).
International Search Report and Written Opinion for PCT/IB2021/053658 mailed Sep. 14, 2021 (15 pages).
International Search Report and Written Opinion for PCT/IB2021/053659 mailed Jul. 22, 2021 (9 pages).
International Search Report and Written Opinion for PCT/IB2021/053660 mailed Aug. 12, 2021 (10 pages).
International Search Report and Written Opinion for PCT/IB2021/054693 mailed Nov. 17, 2021 (7 pages).
International Search Report and Written Opinion for PCT/IB2022/052377 mailed Jun. 30, 2022 (8 pages).
International Search Report and Written Opinion for PCT/IB2022/052651 mailed Jul. 1, 2022 (11 pages).
International Search Report and Written Opinion for PCT/IB2022/059058 mailed Feb. 16, 2023 (8 pages).
International Search Report and Written Opinion for PCT/IB2022/059238 mailed Feb. 24, 2023 (12 pages).
International Search Report and Written Opinion for PCT/IB2022/059239 mailed Feb. 14, 2023 (7 pages).
International Search Report and Written Opinion for PCT/IB2022/059240 mailed Feb. 23, 2023 (13 pages).
International Search Report and Written Opinion for PCT/IB2022/059648 mailed Feb. 21, 2023 (8 pages).
International Search Report and Written Opinion for PCT/IB2022/059649 mailed Feb. 7, 2023 (8 pages).
International Search Report and Written Opinion for PCT/IB2022/062426 mailed Jun. 6, 2023 (8 pages).
International Search Report and Written Opinion for PCT/IB2023/052862 mailed Jul. 27, 2023 (8 pages).
Jing et al., "Separation of monocloncal antibody charge variants using cation exchange chromatography: Resins and separation conditions optimization", Separation and Purification Technology, vol. 235, Mar. 18, 2020.
Khawli et al., "Charge variants in IgG1: Isolation, characterization, in vitro binding properties and pharmacokinetics in rats", Mabs, Nov.-Dec. 2010, 2(6):613-24. doi: 10.4161/mabs.2.6.13333. (12 pages).
Lacher et al. (2010) "Development, validation, and implementation of capillary gel electrophoresis as a replacement for SDSPAGE for purity analysis of lgG2," mAbs, J. Sep. Sci. 33:218-227.
Lee et al. (2010) "Capillary Electrophoretic Separation of Poly(ethylene glycol)-Modified Granulocyte-Colony Stimulating Factor," Arch Pharm Res 22(3)491-495.
Liu et al. (2005) "Highly efficient approach for characterizing nanometer-sized gold particles by capillary electrophoresis," Analytica Chimica Acta 528: 249-254.
Lou et al., "Liquid-liquid phase separation causes high turbidity and pressure during low pH elution process in Protein A chromatography", Journal of Chromatography, Jan. 28, 2017, vol. 1488, pp. 57-67. (11 pages).
Lui et al. "(2010) Recovery and purification process development for monoclonal antibody production," mAbs 2(5):480-499.
Martias, et al. (2021) "Optimization of Sample Preparation for Metabolomics Exploration of Urine, Feces, Blood and Saliva in Humans Using Combined NMR and UHPLC-HRMS Platforms," Molecules 26(4111) 16 pages.
Molecular Probes, Protein Molecular Weight Standards (P-6649), Jan. 13, 2001, pp. 1-2.
Padfield, et al. (1986) "Separation of Guinea-Pig Pancreatic Juice Proteins by Reversed-Phase High-Performance Liquid Chromatography," Journal of Chroma. 369:133-141.
R&D Systems, Inc., "Recombinant Human CTLA 4 Fc Chimera | Catalog No. 7268-CT". Product datasheet (online). Mar. 6, 2020. (2 pages).
Sanger-van de Griend et al. (2019) "CE-SOS method development, validation, and best practice—An overview," Electrophoresis 40:2361-2374.
Shekhawat et al., "Structural similarity, characterization of Poly Ethylene Glycol linkage and identification of product related variants in biosimilar pegfilgrastim", 1-33, Plos One Web. Mar. 13, 2019. (33 pages).
Singla et al., "Aggregation Kinetics for IgG1-Based Monoclonal Antibody Therapeutics", AAPS J., May 2016, 18(3):689-702. doi: 10.1208/s12248-016-9887-0. (14 pages).
Sobczak et al., "RNA structure analysis assisted by capillary electrophoresis", Nucleic Acids Research, Nov. 15, 2002, vol. 30, No. 22, e124. (8 pages).
Somerville et al. (1999) "Discrimination of granulocyte colony-stimulating factor isoforms by high-performance capillary electrophoresis," Journal of Chromatography B, 732:81-89.
Turner et al., "Development of orthogonoal NISTmAb size heterogeneity control methods", Analytical and Bioanalytical Chemistry, Mar. 2018, vol. 410, No. 8, pp. 2095-2110. (16 pages).
Voitl et al. (2010) "Application of mixed mode resins for the purification of antibodies," Journal of Chromatography A 1217:5753-5760.
Yang et al. (2015) "High resolution separation of recombinant monoclonal antibodies by size-exclusion ultra-high performance liquid chromatography (SE-UHPLC)," Journal of Pharmaceutical and Biomedical Analysis 109:52-61.
Degterev et al. (2011) "Improvement of the Degradation Profiling of Eculizumab and Omalizumab Monoclonal Antibodies by Liquid Chromatography-Mass Spectrometry," Journal of Analytical Chemistry 76(14):1596-1609.
Ichiuhara et al. (2018) "Integrated flow-through purification for therapeutic monoclonal antibodies processing," MABS 10(2):325-334.
Phenomenex: "High Performance Size Exclusion for Biomolecules," Oct. 4, 2010 (Oct. 4, 2010), XP093277516, Retrieved from the Internet: URL:https://phenomenex.blob.core.windows.net/documents/7b9fe422-933e-48df-a189-373e2 ef59503.pdf.
Wang et al. Characterization and pre-clinical assessment of a proposed biosimilar to its originator Omalizumab, Eur. J. Pharm Sci 178(1):106292 (2022).
Weisbjerg et al. (2015) "Serial Coupling of Ion-Exchange and Size-Exclusion Chromatography to Determine Aggregation Levels in mAbs in the Presence of a Proteinaceous Excipient, Recombinant Human Serum Albumin," Journal of Pharmaceutical Sciences 104:548-556.
XOLAI R® (omalizumab) product insert https://www.accessdata.fda.gov/drugsatfda_docs/label/2023/103976s5242lbl.pdf 2003.
XOLAIR® (omalizumab) injection for subcutaneous use [package insert]. Accessdata.fda.gov. 2021. https:// www.accessdata.fda.gov/drugsatfda_docs/label/2021/103976s5238lbl.pdf (Year: 2021).

* cited by examiner

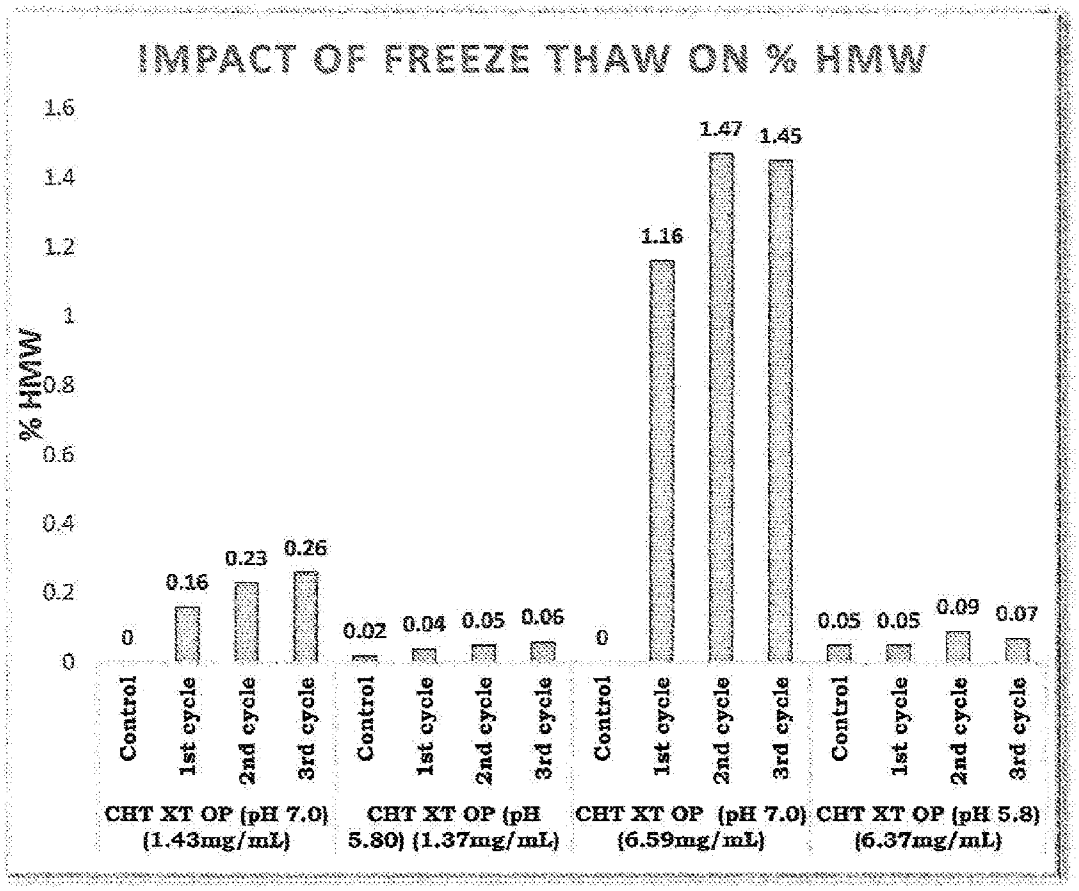
Impact of freeze thaw on aggregation in protein pre-formulation

PROCESS OF STORING AND PREPARING THE PROTEIN

CROSS-REFERENCE TO RELATED APPLICATIONS

This application is a U.S. National Phase Application under 35 U.S.C. § 371 of International Patent Application No. PCT/I1B2021/054693, filed May 28, 2021, which claims the benefit of and priority to Indian Patent Application No. 202021022374, filed on May 28, 2020, each of which is incorporated by reference herein in its entirety.

FIELD OF THE INVENTION

The present invention provides a method for reducing the protein aggregation by adjusting the pH below 6.0 of liquid pre-formulation comprising the antibody or fusion protein wherein the pre-formulation is capable to formulate in final formulation. The present invention also provides methods for storing the pre-formulation for longer period without using any sugar or additives.

BACKGROUND OF THE INVENTION

Monoclonal antibodies as a class of therapeutic molecules are finding an increasing demand in the biotechnology industry for the treatment of diseases. The process of monoclonal antibody development and, specifically, formulation development is a critical bottleneck on the way from candidate selection to fully commercialized medicines. A key challenge associated to successful commercialization of antibodies are that from the various physical and chemical instabilities that are inherent to these molecules. In clinical practice, several mAb products have been approved by regulatory entities, but their formulations have been highly specific given the complex structure and proteinaceous nature of mAbs. Thus, more attention has been given on formulations. Another challenge associated with the commercialization is the cost of the antibodies which also depends over the development of formulations. Usually lyophilized or Liquid formulation require different drug substance preparation and therefore it is time consuming and expensive.

There is a present need for methods of producing formulation comprising an antibody or fusion proteins which can be stored at pH between 5.5 to 5.8 without addition of any sugar or stabilizer for at least 12 hours at frozen temperature and can be utilized further by performing freeze and thaw for the preparation of liquid or lyophilized formulation.

SUMMARY OF THE INVENTION

In an embodiment, the present invention provides a method for reducing the pH induced protein aggregation during freeze thaw cycle liquid formulation comprising an antibody which is stored at freezing temperature at suitable pH for at least 24 hours.

In an embodiment, the present invention provides a method for reducing the concentration induced protein aggregation during freeze thaw cycle liquid formulation comprising an antibody which is stored at freezing temperature at suitable pH for at least 24 hours.

In an embodiment, the present invention provides a method for reducing the pH induced protein aggregation during freeze thaw cycle liquid formulation comprising an antibody which is stored at freezing temperature at suitable pH for at least 7 days.

In one aspect of this embodiment, the present invention provides suitable pH selected from 5.0, 5.1, 5.2, 5.3, 5.4, 5.5, 5.6, 5.7, 5.8, and 5.9.

In one aspect of this the present invention provides method for reducing the pH induced protein aggregation during freeze thaw cycle selected from first cycle or at second cycle or third cycle or four cycle or five cycle or six cycle or seven cycle or eight cycle or nine cycle or ten cycle.

In an embodiment, the invention provides a process for the preparation of stable formulation comprising:

- a. Pre-formulation capable to formulate in lyophilized or liquid formulation comprising;
  - i. An antibody of interest;
  - ii. Suitable buffer;
  - iii. Suitable pH;
- b. Adjusting the pH of pre-formulation to about pH 5.0 to about 5.9;
- c. Optionally performing ultrafiltration;
- d. Storing the pre-formulation at freezing temperature for suitable period of time; e. Performing the freeze thaw cycle of pre-formulation;
- f. Mixing the suitable excipients in pre-formulation to formulate final formulation.

Wherein the pre-formulation comprises substantially low aggregates or High molecular weight impurities after the storage at frozen temperature.

In an embodiment, the invention provides method of storing and using for the preparation of the final formulation comprising:

- a. Pre-formulation comprising:
  - i. An antibody of interest,
  - ii. Suitable buffer,
  - iii. pH 6.0 to 7.0;
- b. Adjusting the pH of pre-formulation to pH 5.5 to 5.8;
- c. Optionally performing ultrafiltration;
- d. Storing the pre-formulation at frozen temperature for suitable period of time;
- e. Performing the freeze thaw cycle of pre-formulation for the preparation of final formulation;
- f. Mixing the suitable excipients in pre-formulation to prepare final formulation.

Wherein the pre-formulation comprises substantially low aggregates after the storage at frozen temperature.

In one aspects of the embodiment, the final formulation is selected from lyophilized formulation or liquid formulation.

In an embodiment, the invention provides pre-formulation comprising:

- a. An antibody of interest;
- b. Suitable buffer;
- c. pH 6.0 to 7.0;
- d. Adjusting the pH of pre-formulation to pH 5.5 to 5.8;
- e. Optionally performing ultrafiltration;
- f. Storing the pre-formulation at frozen temperature for suitable period of time;
- g. Performing the freeze thaw cycle of pre-formulation.

Wherein the pre-formulation comprises substantially low aggregates during freeze thaw cycle after storing at frozen temperature compared to pre-formulation stored at pH higher than 5.5 to 5.8.

In an embodiment, the invention provides pre-formulation enriched antibody of interest and substantially reduced aggregates or HMW comprises about 0.1% or less. In one aspect of this embodiment, the low aggregates or HMW composition comprises about 0.09% or less, 0.08% or less, 0.07% or less, 0.06% or less, 0.05% or less, 0.04% or less and 0.03% or less.

In an embodiment, the pre-formulation is stored and first cycle of freeze thaw is performed by suitable period selected from at least by 1 day, 2, days, 3 days, 4, days, 5 days, 6 days, 7 days, 8 days, 9 days, 10 days, 11 days, 12 days, 13 days, 14 days, 15 days, 16 days, 17 days, 18 days, 19 days, 20 days, 21, days, 22 days, 23 days, 24 days, 25 days, 26 days, 27 days, 28 days, 29 days, 30 days, 40 days, 50 days, 60 days, 90 days, 120 days.

In an embodiment, the pre-formulation is stored and second or any subsequent cycle of freeze thaw is performed by suitable period selected from at least by 12 hours, 24 hours, 30 hours, 40 hours, 50 hours, 60 hours, 72 hours, 84 hours, 96 hours, 108 hours, 120 hours, 7 days, 10 days, 15 days, 20 days, 25 days, 30 days, 40 days, 50 days, 60 days, 3 months, 4 months, 5 months, 6 months, 7 months, 8 months, 9 months, 10 months, 11 months, 12 months.

BRIEF DESCRIPTION OF THE INVENTION

FIG. 1 depicts the impact of freeze thaw on aggregation in protein pre-formulation.

DETAIL DESCRIPTION OF THE INVENTION

The term "comprises" or "comprising" is used in the present description, it does not exclude other elements or steps. For the purpose of the present invention, the term "consisting of" is considered to be an optional embodiment of the term "comprising of". If hereinafter a group is defined to comprise at least a certain number of embodiments, this is also to be understood to disclose a group which optionally consists only of these embodiments.

As used throughout the specification and in the appended claims, the singular forms "a," "an," and "the" include the plural reference unless the context clearly dictates otherwise.

The term "about", as used herein, is intended to refer to ranges of approximately 10-20% greater than or less than the referenced value. In certain circumstances, one of skill in the art will recognize that, due to the nature of the referenced value, the term "about" can mean more or less than a 10-20% deviation from that value.

The term "antibody" includes an immunoglobulin molecule comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region (CH). The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, and FR4.

Omalizumab (Xolair®) is a recombinant DNA-derived humanized IgG1K monoclonal antibody that selectively binds to human immunoglobulin (IgE). The antibody has a molecular weight of approximately 149 kD. Xolair® is produced by a Chinese hamster ovary cell suspension culture in a nutrient medium containing the antibiotic gentamicin. Gentamicin is not detectable in the final product. Xolair® is a sterile, white, preservative-free, lyophilized powder contained in a single-use vial that is reconstituted with Sterile Water for Injection (SWFI), USP, and administered as a subcutaneous (SC) injection. Xolair® injection is supplied as a sterile, preservative-free, clear to slightly opalescent and colorless to pale brownish-yellow solution for subcutaneous injection available as a single-dose prefilled syringe.

The term "Anion exchange chromatography" or "anion exchange column" or "AEX" is a form of ion exchange chromatography (IEX), which is used to separate molecules based on their net surface charge. Anion exchange chromatography, more specifically, uses a positively charged ion exchange resin with an affinity for molecules having net negative surface charges. Anion exchange chromatography is used both for preparative and analytical purposes and can separate a large range of molecules, from amino acids and nucleotides to large proteins. Here, we focus on the preparative anion exchange chromatography of proteins.

The term "POROS 50 HQ" used herein is a Thermo Scientific™ POROS™ Strong Anion Exchange Resins (POROS AEX resins) are designed for charge-based chromatographic separation of biomolecules including recombinant proteins, monoclonal antibodies. Thermo Scientific™ POROS™ 50 HQ resin is functionalized with quaternized polyethyleneimine groups.

When "strong anion exchange" is used in flow through process the equation changes, the impurities are differentiated from the protein of interest, i.e., strong anion exchange is generally known for removal of protein A contaminant, HCP, DNA or virus in antibody purification. In a flow-through protocol, the sample and equilibration buffer are adjusted to conditions where contaminant molecules will still bind to the resin, but the protein of interest will not (because of the charge). This is achieved by increasing the salt concentration and/or increasing the pH of the buffers to a point below the pI of your molecule of interest.

As used herein the term "flow-through mode" or "flow-through" refers to purification process wherein antibody of interest does not bind to chromatography resin. In certain embodiment, the at least 50% antibody of interest does not bind to chromatographic resin. In certain embodiment, the at least 60% or 70% or 80% antibody of interest does not bind to chromatographic resin. However, process and product related impurities bind the chromatographic resin. In certain embodiment, the at least 50% process and product related impurities bind to chromatographic resin. In certain embodiment, the at least 60% or 70% or 80% process and product related impurities bind to chromatographic resin.

The term "CHT" or "Ceramic Hydroxyapatite Chromatography" is a form of calcium phosphate used in the chromatographic separation of biomolecules. Sets of five calcium doublets (C-sites) and pairs of —OH containing phosphate triplets (P-sites) are arranged in a repeating geometric pattern. Repeating hexagonal structures can be seen in electron micrographs of the material. Space-filling models and repeat structure from Raman spectroscopy have also been constructed.

Hydroxyapatite has unique separation properties and unparalleled selectivity and resolution. It often separates proteins shown to be homogeneous by electrophoretic and other chromatographic techniques.

Applications of hydroxyapatite chromatography include the purification of different subclasses of monoclonal and polyclonal antibodies, antibodies that differ in light chain composition, antibody fragments, isozymes, supercoiled DNA from linear duplexes, and single-stranded from double stranded DNA. CHT ceramic hydroxyapatite is a spherical, macroporous form of hydroxyapatite. It has been sintered at high temperatures to modify it from a crystalline to a ceramic form.

The term used "high molecular weight or HMW" is product-related impurities that contribute to the size heterogeneity of antibody products. The formation of HMW species within a therapeutic antibody drug product as a result of protein aggregation can potentially compromise both drug efficacy and safety (e.g., eliciting unwanted immunogenic response). HMW is considered critical quality attributes that are routinely monitored during drug development and as part of release testing of purified drug product during manufacturing.

The term used "aggregates" are classified based on types of interactions and solubility. Soluble aggregates are invisible particles and cannot be removed with a filter. Insoluble aggregates can be removed by filtration and are often visible to the human eye. Both types of aggregates cause problems in biopharma development. Covalent aggregates arise from the formation of a covalent bond between multiple monomers of a given peptide. Disulfide bond formation of free thiols is a common mechanism for covalent aggregation. Oxidation of tyrosine residues can lead to formation of bityrosine which often results in aggregation. Reversible protein aggregation typically results from weaker protein interactions they include dimers, trimers, multimers among others.

The term used "substantially reduced aggregates or HMW" relates to evaluation or detection of aggregates or HMW in pre-formulation through techniques known in the art. In embodiment, the aggregates or HMW present in pre-formulation below about 0.1% or less evaluated through SEC-HPLC. In certain embodiment, the low aggregates or HMW present in pre-formulation below about 0.09% or less, 0.08%, 0.07% evaluated through SEC-HPLC.

As used herein, the term "antioxidant" is intended to mean an agent which inhibits oxidation and thus is used to prevent the deterioration of preparations by the oxidative process. Such compounds include by way of example and without limitation, acetone, sodium bisulfate, ascorbic acid, ascorbyl palmitate, citric acid, butylated hydroxyanisole, butylated hydroxytoluene, hydrophosphorous acid, monothioglycerol, propyl gallate, methionine, sodium ascorbate, sodium citrate, sodium sulfide, sodium sulfite, sodium bisulfite, sodium formaldehyde sulfoxylate, thioglycolic acid, sodium metabisulfite, EDTA (edetate), pentetate and others known to those of ordinary skill in the art.

As used herein, the term "bulking agent" is intended to mean a compound used to add bulk to the reconstitutable solid and/or assist in the control of the properties of the formulation during preparation. Such compounds include, by way of example and without limitation, dextran, trehalose, sucrose, polyvinylpyrrolidone, lactose, inositol, sorbitol, dimethylsulfoxide, glycerol, albumin, calcium lactobionate, and others known to those of ordinary skill in the art.

The term "cryoprotectants" as used herein generally includes agents, which provide stability to the protein from freezing-induced stresses. Examples of cryoprotectants include polyols such as, for example, mannitol, and include saccharides such as, for example, sucrose, as well as including surfactants such as, for example, polysorbate, poloxamer or polyethylene glycol, and the like. Cryoprotectants also contribute to the tonicity of the formulations.

As used herein, the terms "ultrafiltration" or "UF" refers to any technique in which a solution or a suspension is subjected to a semi-permeable membrane that retains macromolecules while allowing solvent and small solute molecules to pass through. Ultrafiltration may be used to increase the concentration of macromolecules in a solution or suspension. In a preferred embodiment, ultrafiltration is used to increase the concentration of a protein in water.

As used herein, the term "diafiltration" or "DF" is used to mean a specialized class of filtration in which the retentate is diluted with solvent and re-filtered, to reduce the concentration of soluble permeate components. Diafiltration may or may not lead to an increase in the concentration of retained components, including, for example, proteins. For example, in continuous diafiltration, a solvent is continuously added to the retentate at the same rate as the filtrate is generated. In this case, the retentate volume and the concentration of retained components does not change during the process. On the other hand, in discontinuous or sequential dilution diafiltration, an ultrafiltration step is followed by the addition of solvent to the retentate side; if the volume of solvent added to the retentate side is not equal or greater to the volume of filtrate generated, then the retained components will have a high concentration. Diafiltration may be used to alter the pH, ionic strength, salt composition, buffer composition, or other properties of a solution or suspension of macromolecules.

As used herein, the terms "diafiltration/ultrafiltration" or "DF/UF" refer to any process, technique or combination of techniques that accomplishes ultrafiltration and/or diafiltration, either sequentially or simultaneously.

A "stable" formulation is one in which the protein therein essentially retains its physical stability and/or chemical stability and/or biological activity upon storage. Various analytical techniques for measuring protein stability are available in the art. The formulation has monomer more than 80% after 12 hours, 24 hours, 3 days, 10 days, 1 month, 3 months, 6 months, 9 months, 12 months, 18 months, 24 months.

The term "stabilizing agent" refers to an excipient that improves or otherwise enhances stability.

Stabilizing agents include, but are not limited to, u-lipoic acid, u-tocopherol, ascorbyl palmitate, benzyl alcohol, biotin, bisulfites, boron, butylated hydroxyanisole (BHA), butylated hydroxytoluene (BHT), ascorbic acid and its esters, carotenoids, calcium citrate, acetyl-L-camitine, chelating agents, chondroitin, chromium, citric acid, coenzyme Q-10, cysteine, cysteine hydrochloride, 3-dehydroshikimic acid (DHS), EDTA (ethylenediaminetetraacetic acid; edetate disodium), ferrous sulfate, folic acid, fumaric acid, alkyl gallates, garlic, glucosamine, grape seed extract, gugul, magnesium, malic acid, metabisulfite, N-acetyl cysteine, niacin, nicotinomide, nettle root, ornithine, propyl gallate, pycnogenol, saw palmetto, selenium, sodium bisulfite, sodium metabisulfite, sodium sulfite, potassium sulfite, tartaric acid, thiosulfates, thioglycerol, thiosorbitol, tocopherol and their esters, e.g., tocopheral acetate, tocopherol succinate, tocotrienal, d-α-tocopherol acetate, vitamin A and its esters, vitamin B and its esters, vitamin C and its esters, vitamin D and its esters, vitamin E and its esters, e.g., vitamin E acetate, zinc, and combinations thereof.

The term "surfactants" generally includes those agents that protect the protein from air/solution interface-induced stresses and solution/surface induced-stresses. For example, surfactants may protect the protein from aggregation. Suitable surfactants may include, e.g., polysorbates, polyoxyethylene alkyl ethers such as Brij 35@, or poloxamer such as Tween 20, Tween 80, or poloxamer 188. Preferred detergents are poloxamers, e.g., Poloxamer 188, Poloxamer 407; polyoxyethylene alkyl ethers, e.g., Brij 35@, Cremophor A25, Sympatens ALM/230; and polysorbates/Tweens, e.g., Polysorbate 20, Polysorbate 80, and Poloxamers, e.g., Poloxamer 188, and Tweens, e.g., Tween 20 and Tween 80.

As used herein, the term "tonicity modifier" is intended to mean a compound or compounds that can be used to adjust the tonicity of a liquid formulation. Suitable tonicity modifiers include glycerin, lactose, mannitol, dextrose, sodium chloride, magnesium sulfate, magnesium chloride, sodium sulfate, sorbitol, trehalose, sucrose, raffinose, maltose and others known to those or ordinary skill in the art. In one embodiment, the tonicity of the liquid formulation approximates that of the tonicity of blood or plasma.

As used herein, the term "diafiltration step" refers to a total volume exchange during the process of diafiltration.

The term "Lyophilization" is refer to stabilizing process in which a substance is first frozen and then the quantity of the solvent is reduced, first by sublimation (the primary drying process) and then desorption (the secondary drying process) to values that will no longer support biological activity or chemical reactions. In a lyophilized formulation, the hydrolysis, deamidation, oxidation and fragmentation reactions associated with solutions can be avoided or slowed significantly. A lyophilized formulation may also avoid damage due to short-term temperature fluctuations during shipping and allow for room temperature storage. The formulations of the present invention may also be dried by other methods known in the art such as spray drying and bubble drying. Unless otherwise specified, the formulations of the present invention are described in terms of their component concentrations as measured in the formulation before lyophilization.

The term "lyoprotectant" refers to a compound that protects against the stresses associated with lyophilization. Therefore, lyoprotectants as a class include cryoprotectants, which just protect from the freezing process. One or more lyoprotectants may be used to protect from the stresses associated with lyophilization and may be, for example, a sugar such as sucrose, raffinose, trehalose; an amino acid such as monosodium glutamate or histidine; a methylamine such as betaine; a lyotropic salt such as magnesium sulfate; a polyol such as trihydric or higher sugar alcohols, e.g. glycerin, erythritol, glycerol, arabitol, xylitol, sorbitol, and manmitol; propylene glycol; polyethylene glycol; Pluronics; and combinations thereof.

The term "pharmaceutical formulation" and "composition" are used interchangeably.

The term "aggregation inhibitor" refers to excipient which prevent aggregation of anti-IgE antibody such as Omalizumab. Aggregation inhibitor is generally useful to stabilize when used in high concentration in the formulation. The suitable aggregation inhibitor is arginine or lysine. However, the selection of aggregation inhibitor in combination with suitable excipients such as buffer, surfactant and pH provide desirable result. The present invention provides desired result when arginine or it's salt like arginine HCl is used with phosphate buffer and poloxamer 188 at pH 6.0. Alternatively, the present invention provides desired result when lysine or it's salt like lysine HCl is used with phosphate buffer or histidine buffer and poloxamer 188 at pH 6.0.

The term "aggregation inhibitor" and "stabilizer" are used interchangeably.

The term used "pre-formulation" herein relates to protein or antibody composition or formulation eluted from the chromatographic column and can be used for the preparation of pharmaceutically acceptable formulation. In embodiment, the pre-formulation means an antibody composition eluted from chromatographic column selected from ion exchange, anion exchange, cation exchange, mixed-mode chromatography, hydrophobic exchange chromatography, ceramic hydroxyapatite chromatography (CHT). In certain embodiment, the pre-formulation comprises purified antibody of interest and suitable buffer at suitable pH. In certain embodiment, buffer and pH of the pre-formulation is similar or identical to elution buffer used during the elution from said chromatographic column. In certain embodiment, buffer and pH of the pre-formulation is not similar to elution buffer used during the elution from said chromatographic column. In certain embodiment, the pH of the pre-formulation is about pH 6 to about pH 7 which is adjusted to below pH 6 before storage. In such embodiment, the pre-formulation comprises substantially low aggregates or high molecular weight 0.1% or less compared to pre-formulation storage at pH 7. In an embodiment, the pre-formulation does not comprise excipients selected from sugar or sugar alcohol, sucrose, mannitol, trehalose, and sorbitol. In another embodiment, the pre-formulation is free of any amino acid except histidine which is used as buffer.

In preferred embodiment, the pre-formulation is free of any amino acid selected from arginine, lysine, glycine.

In other embodiment, the pre-formulation is further treated with ultrafiltration to concentrate the protein.

The term used "frozen temperature" herein relates to freezing temperature suitable to store pre-formulation selected from 0° C. to −80° C., −10° C., −20° C., −30° C., −40° C., −50° C., −60° C., −70° C., or −80° C. In certain embodiment, the frozen temperature is selected from 0° C. to −20° C. In an embodiment, the frozen temperature is −20° C.

The term used "final formulation" herein relates to pharmaceutically acceptable formulation comprises pre-formulation obtained after freeze thaw cycle and at least one additional excipient. In certain embodiment, the final formulation is liquid formulation. In certain embodiment, the final formulation is lyophilized formulation.

As used herein, "buffer" refers to a buffered solution that resists changes in pH by the action of its acid-base conjugate components. The buffer of this invention has a pH in the range from about 3.0 to about 8.5; preferably from about pH 5.0 to about 7.0. In certain embodiment the buffer maintains the pH of pre-formulation from about 6 to about pH 7. In certain embodiment the buffer maintains the pH of pre-formulation from about 5 to about pH 5.9 preferably 5.5 to 5.8.

The term used "high salt buffer" refers to high strength or high molality buffer.

The term used "buffer A" and "buffer B" is interchangeable with "first buffer" or "second buffer" respectively in CHT chromatography.

In an embodiment, the pre-formulation is stored for suitable period selected from at least by 12 hours, 24 hours, 30 hours, 40 hours, 50 hours, 60 hours, 72 hours, 84 hours, 96 hours, 108 hours, 120 hours, 7 days, 10 days, 15 days, 20 days, 25 days, 30 days, 40 days, 50 days, 60 days, 3 months, 4 months, 5 months, 6 months, 7 months, 8 months, 9 months, 10 months, 11 months, and 12 months.

In an embodiment, the present invention provides a method for reducing the pH induced protein aggregation during freeze thaw cycle liquid formulation comprising an antibody which is stored at freezing temperature at suitable pH for at least 12 hours.

In one aspect of this embodiment, the present invention provides suitable pH selected from 5.0, 5.1, 5.2, 5.3, 5.4, 5.5, 5.6, 5.7, 5.8 and 5.9.

In preferred embodiment, the pH is from about 5.5 to about 5.8.

In one aspect of this the present invention provides method for reducing the pH induced protein aggregation during freeze thaw cycle selected from first cycle or at second cycle or third cycle or four cycle or five cycle or six cycle or seven cycle or eight cycle or nine cycle or ten cycle.

In an embodiment, the invention provides a process for the preparation of stable formulation comprising:

a. Pre-formulation capable to formulate in lyophilized or liquid formulation comprising;
   i. An antibody of interest;
   ii. Suitable buffer;
   iii. Suitable pH;
b. Adjusting the pH of pre-formulation to about pH 5.0 to about 5.9;
c. Optionally performing ultrafiltration;
d. Storing the pre-formulation at freezing temperature for suitable period of time;
e. Performing the freeze thaw cycle of pre-formulation;
f. Mixing the suitable excipients in pre-formulation to formulate final formulation.

Wherein the pre-formulation comprises substantially low aggregates or High molecular weight impurities after the storage at frozen temperature.

In an embodiment, the invention provides method of storing and using for the preparation of the final formulation comprising:

a. Pre-formulation comprising:
   i. An antibody of interest,
   ii. Suitable buffer,
   iii. pH 6.0 to 7.0;
b. Adjusting the pH of pre-formulation to pH 5.5 to 5.8;
c. Optionally performing ultrafiltration;
d. Storing the pre-formulation at frozen temperature for suitable period of time;
e. Performing the freeze thaw cycle of pre-formulation for the preparation of final formulation;
f. Mixing the suitable excipients in pre-formulation to prepare final formulation.

Wherein the pre-formulation comprises substantially low aggregates after the storage at frozen temperature.

In one aspects of the embodiment, the final formulation is selected from lyophilized formulation or liquid formulation.

In an embodiment, the invention provides pre-formulation comprising:

a. An antibody of interest;
b. Suitable buffer;
c. pH 6.0 to 7.0;
d. Adjusting the pH of pre-formulation to pH 5.5 to 5.8;
e. Optionally performing ultrafiltration;
f. Storing the pre-formulation at frozen temperature for suitable period of time;
g. Performing the freeze thaw cycle of pre-formulation.

Wherein the pre-formulation comprises substantially low aggregates during freeze thaw cycle after storing at frozen temperature compared to pre-formulation stored at pH higher than 5.5 to 5.8.

In an embodiment, the invention provides an improved method of storing and utilizing pre-formulation which can be stored for longer time and substantially low aggregation or HMW was observed during freeze thaw cycle wherein the pre-formulation is free of any sugar or sugar alcohol, sucrose, mannitol, trehalose, and sorbitol. In another embodiment, the pre-formulation is free of any amino acid except histidine which is used as buffer.

In preferred embodiment, the pre-formulation is free of any amino acid selected from arginine, lysine, and glycine. Low amount of HMW or aggregation after storing a period of time at pH 5.5 to 5.8 makes the pre-formulation suitable to be used for the preparation of final formulation which pharmaceutically acceptable and useful to patient. In embodiment, the final formulation is prepared by mixing one or more excipients.

In an embodiment, first cycle of freeze thaw of stored pre-formulation is performed by suitable period selected from at least by 1 day, 2, days, 3 days, 4, days, 5 days, 6 days, 7 days, 8 days, 9 days, 10 days, 11 days, 12 days, 13 days, 14 days, 15 days, 16 days, 17 days, 18 days, 19 days, 20 days, 21, days, 22 days, 23 days, 24 days, 25 days, 26 days, 27 days, 28 days, 29 days, 30 days, 40 days, 50 days, 60 days, 90 days, and 120 days. In embodiment, the first cycle of freeze thaw of stored pre-formulation is performed by 7 days.

In an embodiment, second or any subsequent cycle of freeze thaw of stored formulation is performed by suitable period selected from at least by 12 hours, 24 hours, 30 hours, 40 hours, 50 hours, 60 hours, 72 hours, 84 hours, 96 hours, 108 hours, 120 hours, 7 days, 10 days, 15 days, 20 days, 25 days, 30 days, 40 days, 50 days, 60 days, 3 months, 4 months, 5 months, 6 months, 7 months, 8 months, 9 months, 10 months, 11 months, and 12 months. In embodiment, second or any subsequent cycle of freeze thaw of stored formulation is performed by 48 to 170 hours.

In an embodiment, the present invention provides pre-formulation eluted from CHT column and comprises a purified biosimilar of omalizumab and phosphate buffer at pH 7.0. pH of pre-formulation is adjusted to pH 5.8 and stored at −20° C. for at least 24 hours. Stored pre-formulation is acclimatized to room temperature through freeze thaw method in order to use stored pre-formulation for the preparation of final formulation. It is imperative to evaluate HMW or aggregates in pre-formulation which can be formed during or after storage and must be controlled under desired limit to utilize pre-formulation for the preparation of final formulation. Omalizumab is available as lyophilized and liquid formulation which are different in terms of excipients. The present invention provides a pre-formulation which is further formulated in pharmaceutically acceptable lyophilized or liquid formulation of omalizumab.

In an embodiment, the final formulation is prepared by adding at least one addition excipients mixed in pre-formulation selected from aggregation inhibitor, buffer, stabilizer, sugar, sugar alcohol, and surfactant.

In an embodiment, the aggregation inhibitor is selected from Arginine, or arginine HCl, Lysine or Lysine HCl, glycine, and proline.

In an embodiment, the buffer is selected from phosphate, citrate, phosphate-citrate, histidine, and acetate, and salt thereof.

In an embodiment, the stabilizer is selected from polysorbate and poloxamer.

Additives used in the present invention is selected from sodium chloride, mannitol, sucrose, proline, glycine, sodium acetate, sodium citrate, sodium succinate, sodium phosphate and sodium sulfate.

In certain embodiment, the final formulation of the present invention has pH 5.0 to pH 7.0. In certain embodiment, the final formulation of the present invention has pH 5.5 to pH 6.5. In certain embodiment, the final formulation of the present invention has pH 6.2.

In another embodiment, the final formulation of the present invention has pH 6.0.

In certain embodiment the drug product obtained from chromatographic steps can be considered pre-formulation. In certain embodiment the drug product obtained from chromatographic steps is further subjected to filtration (TFF) to exchange the desired buffer.

The pre-formulation is capable to formulate in liquid or lyophilized formulation.

Liquid and lyophilized formulation can be prepared by skilled person as per knowledge available in the art.

In an embodiment, the pre-formulation is formulated into a final formulation by mixing suitable excipients in pre-formulation, the suitable excipients comprises;

a. buffer selected from phosphate, citrate, phosphate-citrate, histidine and acetate and salt thereof;
b. optionally suitable aggregation inhibitor selected from Arginine or arginine HCl, Lysine or Lysine HCl, glycine and proline;
c. optionally sugar, sugar alcohol;
d. suitable surfactant selected from polysorbate and poloxamer; and
e. pH 6.0 to 7.0;
f. an antibody of interest.

In an embodiment, the pre-formulation is formulated into a final formulation by mixing suitable excipients in pre-formulation, the suitable excipients comprises;

a. buffer selected from phosphate, citrate, phosphate-citrate, histidine and acetate and salt thereof;
b. optionally suitable aggregation inhibitor selected from Arginine or arginine HCl, Lysine or Lysine HCl, glycine and proline;
c. suitable surfactant selected from polysorbate and poloxamer; and
d. pH 6.0 to 7.0;
e. an Antibody of interest.

In an embodiment, the pre-formulation is formulated into a final formulation by mixing suitable excipients in pre-formulation, the suitable excipients comprises;

a. buffer selected from phosphate, citrate, phosphate-citrate, histidine and acetate and salt thereof;
b. optionally sugar, or sugar alcohol;
c. suitable surfactant selected from polysorbate and poloxamer; and
d. pH 6.0 to 7.0;
e. an Antibody of interest.

The sugar or sugar alcohol is selected from sucrose, mannitol, trehalose, sorbitol, and raffinose.

In an embodiment, the pharmacological antibody is present in high concentration selected form 50 mg/ml to 200 mg/ml. In certain embodiment, the pharmacological antibody is present in high concentration selected form 80 mg/ml to 200 mg/ml. In certain embodiment, the pharmacological antibody is present in high concentration selected form 100 mg/ml to 200 mg/ml. In certain embodiment, the pharmacological antibody is present in high concentration selected form 125 mg/ml to 200 mg/ml.

In certain embodiment, the pharmacological antibody is present in high concentration selected form 150 mg/ml.

In certain embodiment, the buffer is presented in the concentration of at least 1 mg/ml. In certain embodiment, the buffer is presented in the range of 1 mg/ml to 10 mg/ml. In certain embodiment, the buffer is presented in the range of 1 mg/ml to 5 mg/ml. In certain embodiment, the buffer is presented in the concentration of 4 mg/ml. In certain embodiment, the buffer is presented in the concentration of 3.7 mg/ml.

In certain embodiment, the aggregation inhibitors are present in the concentration of at least 1 mg/ml. In certain embodiment, the aggregation inhibitors are present in the range of 1 mg/ml to 75 mg/ml. In certain embodiment, the aggregation inhibitors are present in the range of 10 mg/ml to 50 mg/ml. In certain embodiment, the aggregation inhibitors are present in range of 20 mg/ml to 50 mg/ml. In certain embodiment, the aggregation inhibitors are present in range of 30 mg/ml to 45 mg/ml.

In certain embodiment, the surfactant is selected from polysorbate and poloxamer 188. In certain embodiment, the surfactant is selected from different grades of polysorbate such as but not limited to polysorbate 20, polysorbate 40, polysorbate 60, polysorbate 80 or mixture thereof can be used. In certain embodiment, the surfactant is poloxamer 188.

In an embodiment, the final formulation has same pH like pre-formulation. In another embodiment, the final formulation has different pH than pre-formulation. In an embodiment, final formulation pH is 6.0.

In certain embodiment the formulation comprises stabilizing agents include, but are not limited to, α-lipoic acid, α-tocopherol, ascorbyl palmitate, benzyl alcohol, biotin, bisulfites, boron, butylated hydroxyanisole (BHA), butylated hydroxytoluene (BHT), ascorbic acid and its esters, carotenoids, calcium citrate, acetyl-L-camitine, chelating agents, chondroitin, chromium, citric acid, coenzyme Q-10, cysteine, cysteine hydrochloride, 3-dehydroshikimic acid (DHS), EDTA (ethylenediaminetetraacetic acid; edetate disodium), ferrous sulfate, folic acid, fumaric acid, alkyl gallates, garlic, glucosamine, grape seed extract, gugul, magnesium, malic acid, metabisulfite, N-acetyl cysteine, niacin, nicotinomide, nettle root, ornithine, propyl gallate, pycnogenol, saw palmetto, selenium, sodium bisulfite, sodium metabisulfite, sodium sulfite, potassium sulfite, tartaric acid, thiosulfates, thioglycerol, thiosorbitol, tocopherol and their esters, e.g., tocopheral acetate, tocopherol succinate, tocotrienal, d-α-tocopherol acetate, vitamin A and its esters, vitamin B and its esters, vitamin C and its esters, vitamin D and its esters, vitamin E and its esters, e.g., vitamin E acetate, zinc, and combinations thereof.

In certain embodiment the formulation comprises tonicity modifiers include glycerin, lactose, mannitol, dextrose, sodium chloride, magnesium sulfate, magnesium chloride, sodium sulfate, sorbitol, trehalose, sucrose, raffinose, maltose and others known to those or ordinary skill in the art. In one embodiment, the tonicity of the liquid formulation approximates that of the tonicity of blood or plasma.

In an embodiment, the invention provides pre-formulation enriched with omalizumab and substantially reduced aggregates or HMW comprises about 0.1% or less. In one aspect of this embodiment, the low aggregates or HMW composition comprises about 0.09% or less, 0.08%, 0.07%.

In an embodiment, the invention provides method of preparing a pre-formulation comprise;

a. applying the protein mixture comprising an antibody or fragment thereof and impurities onto affinity chromatography column;
b. washing the column with suitable wash buffer;
c. eluting the protein mixture with suitable buffer wherein the eluted protein mixture is enriched with antibody of interest;
d. performing the viral inactivation of protein mixture obtained from step (c);
e. loading the protein mixture obtained from step (d) to anion exchange chromatography column;
f. eluting the protein mixture in flow through mode;

g. optionally regenerating the anion exchange column with a suitable buffer to elute impurities bound to the anion exchange column.

In an embodiment, the protein mixture eluted from anion exchange at pH 7.3 is considered as pre-formulation and stored at frozen temperature after adjusting pH at 5.5-5.8 which is further used for the preparation of final formulation after freeze thaw cycle. Wherein the pre-formulation comprises substantially low aggregates during freeze thaw cycle after storing at frozen temperature compared to pre-formulation stored at pH higher than 5.5 to 5.8.

In an embodiment, the invention provides method of preparing a pre-formulation comprises;

a. applying the protein mixture comprising an antibody or fragment thereof and impurities onto affinity chromatography column;
b. washing the column with suitable wash buffer;
c. eluting the protein mixture with suitable buffer wherein the eluted protein mixture is enriched with antibody of interest;
d. performing the viral inactivation of protein mixture obtained from step (c);
e. loading the protein mixture obtained from step (d) to anion exchange chromatography column;
f. eluting the protein mixture in flow through mode;
g. optionally regenerating the anion exchange column with a suitable buffer to elute impurities bound to the anion exchange column;
h. loading the protein mixture obtained from step (f) onto mixed-mode chromatography;
i. washing the mixed-mode chromatography column with a suitable wash buffer to elute impurities bound to the column;
j. eluting the protein of mixture from mixed-mode chromatography column with suitable buffer.

In an embodiment, the protein mixture eluted from mixed-mode chromatography column is considered as pre-formulation and stored at frozen temperature at pH 5.5-5.8 which is further used for the preparation of final formulation after freeze thaw cycle. Wherein the pre-formulation comprises substantially low aggregates during freeze thaw cycle after storing at frozen temperature compared to pre-formulation stored at pH higher than 5.5 to 5.8.

In an embodiment, the invention provides method of preparing a pre-formulation comprise;

a. applying the protein mixture comprising Omalizumab and impurities onto affinity chromatography column;
b. washing the column with suitable wash buffer;
c. eluting the protein mixture with suitable buffer wherein the eluted protein mixture is enriched with Omalizumab;
d. performing the viral inactivation of protein mixture obtained from step (c);
e. loading the protein mixture obtained from step (d) to anion exchange chromatography column;
f. eluting the protein mixture in flow through mode;
g. optionally regenerating the anion exchange column with a suitable buffer to elute impurities bound to the anion exchange column;
h. loading the protein mixture obtained from step (f) onto mixed-mode chromatography;
i. washing the mixed-mode chromatography column with a suitable wash buffer to elute impurities bound to the column;
j. eluting the protein of mixture from Mixed-mode chromatography column with suitable buffer.

In an embodiment, the protein mixture eluted from mixed-mode chromatography column is considered as pre-formulation enriched with omalizumab and stored at frozen temperature at pH 5.5-5.8 which is further used for the preparation of final formulation after freeze thaw cycle. Wherein the pre-formulation comprises substantially low aggregates during freeze thaw cycle after storing at frozen temperature compared to pre-formulation stored at pH higher than 5.5 to 5.8. In such embodiment, the mixed-mode chromatography is ceramic hydroxy apatite (CHT).

In an embodiment, the protein mixture obtained from affinity chromatography if further subjected to viral inactivation and neutralization thereafter conductivity is adjusted with WFI and pH is adjusted with tris before loading onto AEX.

In an embodiment, antibody is selected from IgG1, IgG2, IgG3, IgG4, and fusion proteins. In certain embodiments, the antibodies are selected from Etanercept (Enbrel®), Rituximab (Rituxan®), Palivizumab (Synagis®), Infliximab (Remicade®), Trastuzumab (Herceptin®), Alemtuzumab (Campath©, Lemtrada®), Adalimumab (Humira®), Ibritumomab tiuxetan (Zevalin®), Omalizumab (Xolair®), Cetuximab (Erbitux®), Bevacizumab (Avastin®), Natalizumab (Tysabri®), Eculizumab (Soliris®), Certolizumab pegol (Cimzia®), Ustekinumab (Stelara©), Canakinumab (Ilaris®), Golimumab (Simponi®), Ofatumumab (Kesimpta®, Arzerra®), Tocilizumab (Actemra®), Denosumab (Prolia®, Xgeva®), Belimumab (Benlysta®), Ipilimumab (Yervoy®), Brentuximab vedotin (Adcetris®), Pertuzumab (Perjeta®), Trastuzumab emtansine (Kadcyla®), Raxibacumab, Obinutuzumab (Gazyva®), Siltuximab (Sylvant®), Ramucirumab (Cyramza®), Vedolizumab (Entyvio®), Blinatumomab (Blincyto®), Nivolumab (Opdivo®), Pembrolizumab (Keytruda®), darucizumab, Necitumumab (Portrazza™), Dinutuximab (Unituxin®), Secukinumab (Cosentyx®), Mepolizumab (Nucala®), Alirocumab (Praluent®), Evolocumab (Repatha®), Daratumumab (Darzalex®), Elotuzumab (Empliciti®), Ixekizumab (Taltz©), Reslizumab (Cingair®), Olaratumab (Lartruvo®), Bezlotoxumab (Zinplava™) Atezolizumab (Tecentriq®), Obiltoxaximab (Anthim®), Sarilumab (Kevzara®), Ocrelizumab (Ocrevus®), Tildrakizumab (Ilumya®), Romosozumab (Evenity®), Brolucizumab (Beovu®), and Crizanlizumab (Adakveo®).

Affinity Chromatography Conditions:

In an embodiment, wherein the affinity chromatography is selected from Protein A or Protein G. In an embodiment, the affinity chromatography resin is selected from Mabselect, Mabselect SuRe, Mabselect SuRe LX, Prosep Ultra Plus, Eshmuno A. In preferred embodiment, the Affinity chromatography resin is Mabselect Sure LX.

In an embodiment, the equilibration buffer or loading buffer or wash buffer is selected from Sodium Phosphate, Tris-HCl, Tris-Acetate, HEPES, and Glycine-NaOH.

In preferred embodiment, the loading buffer is Tris Acetate, or Tris-HCl.

In certain embodiment, the equilibration buffer or loading buffer or wash buffer used in combination with a salt. In certain embodiment, the salt is selected from Sodium Chloride, Potassium Chloride. In preferred embodiment, the salt is Sodium Chloride.

In an embodiment, the equilibration buffer has concentration range from about 5 mM to about 40 mM. In certain embodiment, the equilibration buffer has concentration range from about 10 mM to about 25 mM. In preferred embodiment, the equilibration buffer concentration is about 20 mM.

In certain embodiment, the equilibration buffer or loading buffer or wash buffer optionally comprises a salt selected from about 50 mM to about 400 mM. In an embodiment, the equilibration buffer comprises a salt buffer concentration selected from about 100 mM to about 200 mM. In an embodiment, the equilibration buffer concentration is about 150 mM. In another embodiment, the equilibration buffer concentration is about 100 mM.

In an embodiment, the equilibration buffer or loading buffer or wash buffer has conductivity range from about 10 mS/cm to about 20 mS/cm. In an embodiment, the equilibration buffer or loading buffer or wash buffer conductivity is about 15.0 mS/cm to 18.0 mS/cm. In another embodiment, the equilibration buffer or loading buffer or wash buffer conductivity is about 10.0 mS/cm to 13.0 mS/cm.

In an embodiment, the pH of the equilibration buffer or loading buffer or wash buffer is selected from about 6.5 to about 7.5. In preferred embodiment, the equilibration buffer pH is about 7.0.

In an embodiment, the loading buffer has concentration range from about 5 mM to about 40 mM. In an embodiment, the loading buffer has concentration range from about 10 mM to about 30 mM. In preferred embodiment, the loading buffer concentration is about 20 mM.

In certain embodiment, the affinity chromatography has at least one wash buffer. In another embodiment, the affinity chromatography has three wash buffers.

In an embodiment, the first wash buffer has concentration range from about 5 mM to about 40 mM. In certain embodiment, the first wash buffer has concentration range from about 10 mM to about 25 mM. In preferred embodiment, the first wash buffer concentration is about 20 mM.

In an embodiment, the second wash buffer is selected from sodium phosphate, Tris-HCl, Tris-Acetate, HEPES, and Glycine-NaOH.

In certain embodiment, second wash buffer used in combination with a salt.

In certain embodiment, the salt is selected from sodium chloride, potassium Chloride. In preferred embodiment, the salt is Sodium Chloride.

In an embodiment, the second wash buffer has concentration range from about 5 mM to about 40 mM. In certain embodiment, the second wash buffer has concentration range from about 10 mM to about 25 mM. In preferred embodiment, the second wash buffer concentration is about 20 mM.

In an embodiment, the second wash buffer has a salt buffer concentration range from about 0.5 M to about 1.5 M. In preferred embodiment, the second wash buffer concentration is about 1.0 M.

In an embodiment, the second wash buffer has conductivity range from about 70 mS/cm to about 120 mS/cm. In an embodiment, the second wash buffer has conductivity range from about 80 mS/cm to about 100 mS/cm. In preferred embodiment, the second wash buffer conductivity is about 90 mS/cm.

In an embodiment, the pH of the second wash buffer is selected from about 6.5 to about 7.5. In preferred embodiment, the second wash buffer pH is about 7.0.

In an embodiment, the second wash buffer further comprises a surfactant which is selected from Polysorbate 20, Polysorbate 80, and Triton X-100, In an embodiment, the preferred surfactant is Polysorbate 20.

In an embodiment, the percentage of the surfactant in the second wash buffer is from about 0.01% to about 1%. In preferred embodiment, the surfactant in the second wash buffer is 0.1% (w/v).

In an embodiment, the third wash buffer has concentration range from about 5 mM to about 40 mM. In certain embodiment, the third wash buffer has concentration range from about 10 mM to about 30 mM. In preferred embodiment, the third wash buffer concentration is about 20 mM.

In an embodiment, the third wash buffer has concentration range from about 5 mM to about 40 mM. In certain embodiment, the third wash buffer has concentration range from about 10 mM to about 40 mM. In preferred embodiment, the third wash buffer concentration is about 30 mM.

In an embodiment, the third wash buffer has conductivity range from about 0.5 mS/cm to about 2.5 mS/cm. In preferred embodiment, the third wash buffer conductivity is less than 2.5 mS/cm.

In an embodiment, the pH of the third wash buffer is selected from about 5 to about 6. In preferred embodiment, the third wash buffer pH is about 5.5.

In an embodiment, the elution buffer is selected from Acetic acid, Phosphoric acid, Sodium acetate, and HCl. In preferred embodiment, the elution buffer is Acetic acid.

In an embodiment, the elution buffer is selected from Acetic acid, Phosphoric acid, Sodium acetate, and HCl. In preferred embodiment, the elution buffer is Sodium acetate.

In an embodiment, the elution buffer has concentration range selected from about 25 mM to about 250 mM.

In an embodiment, the elution buffer has concentration range selected from about 100 mM to about 250 mM. In an embodiment, the elution buffer has a concentration range about 125 mM to 200 mM.

In an embodiment, the elution buffer has conductivity range from about 0.2 mS/cm to about 1.0 mS/cm. In an embodiment, the elution buffer has conductivity range from about 0.5 mS/cm to about 1.0 mS/cm. In an embodiment, the elution buffer has conductivity range from about 0.5 mS/cm to about 0.6 mS/cm. In an embodiment, the elution buffer has conductivity range from about 0.2 mS/cm to about 0.3 mS/cm.

In an embodiment, the pH of the elution buffer is selected from 2.5 to about 3.5. In preferred embodiment, the elution buffer pH is about 3.5.

In an embodiment, the elution buffer has conductivity range from about 0.2 mS/cm to about 0.3 mS/cm. In an embodiment, the pH of the elution buffer is selected from 2.5 to about 3.5. In preferred embodiment, the elution buffer pH is about 3.0.

In certain embodiment, elution is performed in linear gradient. In certain embodiment, the elution is performed in step gradient.

In an embodiment, where the elution peak Collection starts at an ascending value of about 2.5 AU/cm and ends at a descending value of about 2.5 AU/cm.

In an embodiment, where the elution peak Collection starts at an ascending value of about 0.25 AU/cm and ends at a descending value of about 0.25 AU/cm.

In an embodiment, the invention provides the antibody composition having a turbidity selected from less than about 100 NTU, less than about 50 NTU, less than about 30 NTU, less than about NTU obtained from Affinity Chromatography wherein the elution buffer has a concentration of about 200 mM.

In another embodiment, the invention provides a purification process of antibodies or fragment thereof by using affinity chromatography wherein the elution is performed at low salt concentration.

In another embodiment, the invention provides a purification process of antibodies or fragment thereof by using affinity chromatography wherein the elution is performed at low salt concentration, which does not reduce the turbidity compared to elution performed with high salt concentration of the of the eluted protein mixture during viral inactivation.

In an embodiment, the equilibration is performed for about 3 CV's to about 10 CV's. In a preferred embodiment, the equilibration is performed for about 5 CV's. In an embodiment, the equilibration is performed until the equilibration buffer conductivity end point is achieved.

In an embodiment, the amount of protein loaded onto the column during loading is at a range of about 10 g/L to about 45 g/L. In an embodiment, the amount of protein loaded onto the column during loading is at a range from about 10 g/L to about 50 g/L.

In an embodiment, the first wash is performed for at least 1 to about 5 CV's. In preferred embodiment the first wash is performed for 3 CV's. In an embodiment, the first wash is performed until the buffer conductivity end point is achieved.

In an embodiment, the second wash is performed for at least 1 CV to about 5 CV's. In preferred embodiment, the second wash is performed for 3 CV's. In an embodiment, the second wash is performed until the buffer conductivity end point is achieved.

In an embodiment, the third wash is performed for at least 4 CV's to about 8 CV's. In preferred embodiment, the third wash is for 5 CV's. In an embodiment, the third wash is performed until the buffer conductivity end point is achieved.

In an embodiment, the residence time of the protein in the column during protein A purification has a range from about 2 minutes to about 6 minutes. In preferred embodiment, the residence time of the protein in the column is about 4 minutes.

AEX Chromatography Conditions:

In an embodiment, the anion exchange chromatography resin is selected from Capto™ Q, DEAE Sepharose fast flow, Fractogel™ EMD DEAE(M), Toyopearl™ DEAE-650, Q Sepharose Fast Flow, POROS™ XQ, POROS™ 50 HQ, POROS™ 50 PI, and POROS™ 50 D. In certain embodiment, the anion exchange chromatography resin is strong anion exchange POROS™ 50 HQ.

In an embodiment, the equilibration buffer or loading buffer is selected from Sodium Phosphate, Tris-HCl, HEPES, Glycine-NaOH, and Tris-Acetate. In certain embodiment, the equilibration buffer or loading buffer is Tris Acetate, or Tris-HCl.

In an embodiment, the equilibration buffer has a concentration range from about 40 mM to about 60 mM. In a certain embodiment, the loading buffer concentration is about 50 mM. In a certain embodiment, the loading buffer concentration is about 20 mM.

In an embodiment, the equilibration buffer has conductivity range from about 1.5 mS/cm to about 3.5 mS/cm. In a certain embodiment, the equilibration buffer conductivity is less than 2.6 mS/cm.

In an embodiment, the pH of the equilibration buffer is selected from about 6.5 to about 7.5. In a certain embodiment, the loading buffer pH is about 7.0 to about 7.5. In an embodiment, the pH of loading buffer is 7.2-7.4.

In certain embodiment, the equilibration buffer conductivity is <2.0 mS/cm.

In an embodiment, the pH of the equilibration buffer is selected from about 6.5 to about 7.5.

In a certain embodiment, the loading buffer pH is about 7.0 to about 7.5. In an embodiment, the pH of loading buffer is 7.2-7.3.

In an embodiment, the loading buffer has a concentration range from about 40 mM to about 60 mM. In a certain embodiment, the loading buffer concentration is about 50 mM.

In an embodiment, the loading buffer has a concentration range from about 10 mM to about 30 mM. In a certain embodiment, the loading buffer concentration is about 20 mM.

In an embodiment, the loading buffer has conductivity range from about 1.5 mS/cm to about 3.5 mS/cm. In a certain embodiment, the loading buffer conductivity is less than 2.6 mS/cm.

In an embodiment, the pH of the loading buffer is selected from about 6.5 to about 7.5.

In certain embodiment, the loading buffer pH is about 7.0 to about 7.5. In an embodiment, the pH of loading buffer is 7.2-7.3.

In certain embodiment, the loading buffer conductivity is about <3.0 mS/cm.

In an embodiment, the pH of the loading buffer is selected from about 6.5 to about 7.5.

In certain embodiment, the loading buffer pH is about 7.0 to about 7.5. In an embodiment, the pH of loading buffer is 7.2-7.3.

In an embodiment, the invention provides protein peak collection criteria selected from the ascending value of about 2.5 AU/cm and ends at a descending value of about 1.5 AU/cm.

In an embodiment, the invention provides protein peak collection criteria selected from the ascending value of about 1.5 AU/cm and ends at a descending value of about 1.5 AU/cm.

In an embodiment, the invention provides the antibody composition comprising antibody of interest and about 10% to 12% acidic variant obtained from AEX chromatography wherein the peak collection criteria is selected from about 2.5 AU/cm to about 1.5 AU/cm.

In another embodiment, the invention provides protein peak collection criteria selected from the ascending value of about 1.5 AU/cm and ends at a descending value of about 1.5 AU/cm.

In an embodiment, the washing buffer is selected from sodium phosphate, Tris-HCl, HEPES, Glycine-NaOH, and Tris-Acetate.

In an embodiment, the washing buffer has concentration range from about 40 mM to about 60 mM. In certain embodiment, the washing buffer concentration is about 50 mM.

In another embodiment, the washing buffer has concentration range from about 10 to about 30 mM. In certain embodiment, the washing buffer concentration is about 20 mM.

In an embodiment, the washing buffer has conductivity range from about 1.5 mS/cm to about 3.5 mS/cm. In preferred embodiment, the washing buffer conductivity is less than 2.6 mS/cm.

In certain embodiment, the washing buffer conductivity is <2.0 mS/cm.

In an embodiment, the pH of the washing buffer is selected from about 6.5 to about 7.5. In certain embodiment the washing buffer pH is about 7.2.

In an embodiment, the regeneration buffer is selected from Sodium Phosphate, Tris-HCl, HEPES, Glycine-NaOH, Tris-Acetate.

In an embodiment, the regeneration buffer has concentration range from about 5 mM to about 30 mM. In certain embodiment, the regeneration buffer concentration is about 20 mM.

In an embodiment, the regeneration buffer also contains a salt selected from Sodium Chloride, Potassium Chloride, and Calcium Chloride. In certain embodiment, the salt in the regeneration buffer is Sodium Chloride.

In an embodiment, the salt in the regeneration buffer has concentration range from about 0.5M to about 1.5 M. In certain embodiment, the salt in the regeneration buffer has concentration of about 1.0 M.

In an embodiment, the regeneration buffer has conductivity range from about 80 mS/cm to about 90 mS/cm. In certain embodiment, the regeneration buffer conductivity is about 85 mS/cm.

In an embodiment, the regeneration buffer has conductivity range from about 90 mS/cm to about 110 mS/cm. In certain embodiment, the regeneration buffer conductivity is about 100 mS/cm.

In an embodiment, the pH of the regeneration buffer is selected from about 6.5 to about 7.5. In preferred embodiment, the regeneration buffer pH is about 7.0.

In an embodiment, the pH of the regeneration buffer is selected from about 6.5 to about 7.5. In preferred embodiment, the regeneration buffer pH is about 7.2.

In an embodiment, the elution is performed in a flow through mode.

In an embodiment, the sanitization buffer is selected from NaOH, Iso-propyl alcohol, benzyl alcohol. In certain embodiment, the sanitization buffer is NaOH.

In an embodiment, the sanitization buffer has concentration range from about 300 mM to about 1500 mM. In certain embodiment, the regeneration buffer concentration is about 500 mM.

In an embodiment, the loading is performed for at least about 5 CV's or more. In a certain embodiment the loading is performed for about 30 CV's.

In an embodiment, the equilibration is performed for at least about 3 CV's to about 10 CV's. In a certain embodiment, the equilibration is performed for about 5 CV's.

In an embodiment, the equilibration is performed until the equilibration buffer conductivity end point is achieved.

In an embodiment, the amount of protein loaded onto the column during loading is selected from less than about 150 g/L, less than about 130 g/L, less than about 120 g/L, less than about 110 g/L, less than about 100 g/L.

In an embodiment, the washing is performed for at least about 5 CV's.

In an embodiment, the washing is performed for at least about 2 CV's.

In an embodiment, the regeneration is performed for at least 2 CV's to about 5 CV's. In a certain embodiment, the regeneration is performed for about 3 CV's.

In an embodiment, the regeneration removes most of the impurities. In preferred embodiment, the regeneration removes most of the HMWs, and acidic charged variant based impurities.

In an embodiment, the sanitization is performed for at least 2 CV's to about 5 CV's. In a certain embodiment, the sanitization is performed for about 3 CV's.

In an embodiment, the sanitization buffer is held in the column for about 15 minutes to about 60 minutes. In certain embodiment, the sanitization buffer is held in the column for about 20 minutes.

In an embodiment, the residence time of the protein in the column during AEX purification has a range from about 2 to about 6 minutes. In a certain embodiment, the residence time of the protein in the column is about 4 minutes.

Ceramic Hydroxy Apatite (CHT) Conditions:

In an embodiment, the mixed-mode chromatography resin (MMC) is selected from from Capto™ adhere (N-Benzyl-N-methyl ethanol amine as ligand), Capto™ MMC (MMC ligand), MEP Hypercel (4-marcaptomethylpyridine as ligand), HEA Hypercel (hexyl amine as ligand), PPA Hypercel (phenylpropylamine as ligand), CHT (Ceramic Hydroxy apatite)—type 1, CHT (Ceramic Hydroxy apatite) Type II.

In certain embodiment, the mixed-mode chromatography resin is CHT (Ceramic Hydroxy apatite)—type 1 and CHT (Ceramic Hydroxy apatite) XT.

In an embodiment, the loading buffer, washing buffer, equilibration buffer and elution buffer is prepared by combining Buffer A and Buffer B.

In certain embodiment, buffer A is polar protic molecule. In certain embodiment, the polar protic molecule is selected from water (H—OH), acetic acid (CH3CO—OH) methanol (CH3-OH), ethanol (CH3CH2-OH), n-propanol (CH3CH2CH2-OH), n-butanol (CH3CH2CH2CH2-OH).

In preferred embodiment, wherein the polar protic molecule is water.

In an embodiment, buffer B is selected from Sodium Phosphate, Tris, HEPES, Glycine-NaOH.

In preferred embodiment, the buffer B is Sodium Phosphate.

In an embodiment, the concentration range of buffer B is from about 10 mM to about 30 mM. In certain embodiment, the concentration of buffer B is about 24 mM.

In an embodiment, the concentration range of buffer B is from about 20 mM to about 40 mM. In certain embodiment, the concentration of buffer B is about 32 mM.

In an embodiment, the concentration range of buffer B is from about 20 mM to about 40 mM. In certain embodiment, the concentration of buffer B is about 40 mM.

In an embodiment, the concentration range of equilibration buffer and loading buffer is from about 20 mM to about 40 mM. In an embodiment, the concentration of equilibration buffer and loading buffer is about 32 mM.

In certain embodiment, the equilibration buffer, loading buffer and wash buffer are same in strength. In an embodiment, the strength of elution buffer is higher than loading buffer.

In an embodiment, the equilibration buffer and loading buffer has concentration range from about 20 to about 50 mM. In certain embodiment, the equilibration buffer concentration is about 40 mM.

In an embodiment, the equilibration buffer has a concentration from about 20 mM to 50 mM. In certain embodiment, the equilibration buffer has a concentration of about 32 mM.

In an embodiment the washing buffer has a concentration from about 10 mM to 30 mM. In certain embodiment the equilibration buffer has a concentration of about 24 mM In an embodiment, the pH of the equilibration buffer or loading buffer or washing buffer or elution buffer is selected from about 6.5 to about 7.5.

In an embodiment, wherein the buffer pH is about 7.0±0.2.

In an embodiment, the equilibration buffer has conductivity range from about 3.0 to about 7.0 mS/cm. In preferred embodiment, the equilibration buffer conductivity is about 6.0 mS/cm.

In an embodiment, the pH of the equilibration buffer is selected from about 6.5 to about 7.5.

In an embodiment, the equilibration buffer pH is about 7.0±0.2.

In an embodiment, the equilibration is performed with isocratic gradient by using combination of at least two buffers where buffer A concentration is at least 10% of buffer B concentration. In preferred embodiment, buffer A concentration is at least 8% of buffer B concentration.

In an embodiment, the loading buffer has concentration range from about 30 to about 60 mM. In preferred embodiment, the loading buffer concentration is about 40 mM.

In an embodiment, the loading buffer has a concentration from about 10 mM to 40 mM. In certain embodiment, the loading buffer has a concentration of about 32 mM.

In an embodiment the loading buffer has a concentration from about 10 mM to 30 mM. In certain embodiment the loading buffer has a concentration of about 24 mM In an embodiment, the loading buffer has conductivity range from about 3.0 to about 7.0 mS/cm.

In preferred embodiment, the loading buffer conductivity is about 6.0 mS/cm.

In an embodiment, the pH of loading buffer is selected from about 6.5 to about 7.5.

In an embodiment, the loading buffer pH is about 7.0±0.2.

In an embodiment, the loading is performed with isocratic gradient by using combination of at least two buffers where buffer A concentration is at least 10% of buffer B concentration. In preferred embodiment, buffer A concentration is at least 8% of buffer B.

In an embodiment, the washing buffer has concentration range from about 30 mM to about 60 mM.

In preferred embodiment, the washing buffer concentration is about 40 mM.

In an embodiment, the washing buffer has a concentration from about 10 mM to 40 mM. In certain embodiment, the washing buffer has a concentration of about 32 mM.

In an embodiment the washing buffer has a concentration from about 10 mM to 30 mM. In certain embodiment the washing buffer has a concentration of about 24 mM In an embodiment, the washing buffer has conductivity range from about 3.0 mS/cm to about 7.0 mS/cm. In preferred embodiment, the washing buffer conductivity is about 6.0 mS/cm.

In an embodiment, the pH of the washing buffer is selected from about 6.5 to about 7.5.

In an embodiment, wherein the washing buffer pH is about 7.0±0.2.

In an embodiment, the washing is performed with isocratic gradient by using combination of at least two buffers where buffer A concentration is at least 10% of, buffer B or less. In preferred embodiment, buffer A concentration is at least 10% of, buffer B concentration.

In an embodiment, the elution buffer has concentration range from about 10 mM to about 400 mM.

In preferred embodiment, the elution buffer has a concentration range from about 32 mM to about 104 mM.

In an embodiment, the elution buffer has concentration range from about 10 mM to about 400 mM.

In preferred embodiment, the elution buffer has a concentration range from about 24 mM to about 100 mM.

In an embodiment, the elution buffer has concentration range from about 10 mM to about 400 mM.

In preferred embodiment, the elution buffer has a concentration range from about 32 mM to about 88 mM.

In an embodiment, the elution buffer has concentration range from about 10 mM to about 400 mM.

In preferred embodiment, the elution buffer has a concentration range from about 40 mM to about 96 mM.

In an embodiment, the elution buffer has conductivity range from about 6 mS/cm to about 12 mS/cm.

In an embodiment the pH of the elution buffer is selected from about 6.5 to about 7.5. In an embodiment, the elution buffer pH is about 7.0±0.2.

In an embodiment, the elution is performed in linear gradient. In certain embodiment, the elution is performed in step gradient.

In an embodiment, the elution is performed with linear gradient by using combination of at least two buffers wherein buffer A concentration is at least 10% of buffer B concentration. In such embodiment, buffer A concentration is at least 10% of buffer B concentration. In such embodiment, buffer B is gradually increased from about 10% to about 24% and optimized concentration of buffer B accordingly.

Moreover, any skilled person will appreciate the minor changes in gradient with respect to run time and particular impurity to be removed.

In such embodiment, elution is performed in isocratic gradient with 15% of buffer B. In such embodiment, elution is performed in isocratic gradient with 20% of buffer B. In such embodiment, elution is performed in isocratic gradient with 15%, 16%, 17%, 18%, 19%, 20% of buffer B.

In another embodiment, the elution is performed with linear gradient by using combination of at least two buffers wherein buffer A concentration is at least 8% of buffer B concentration. In such embodiment, buffer A concentration is at least 8% of, buffer B % concentration. In such embodiment, buffer B is gradually increased from about 8% to about 22% and optimized concentration of buffer B accordingly. In such embodiment, buffer B is gradually increased from about 6% to about 22% and optimized concentration of buffer B accordingly.

In an embodiment, wherein the elution peak collection starts at an ascending value of about 1.5 AU/cm and ends at a descending value of about 2.0 AU/cm for minimising LMWs.

In an embodiment, wherein the elution peak collection starts at an ascending value of about 1.0 AU/cm and ends at a descending value of about 1.5 AU/cm for minimising LMWs.

In certain embodiment, the CHT is performed in bind and elute mode.

In certain embodiment, the CHT is performed with buffer or solvent free from calcium chloride.

In certain embodiment, the concentration of the elution buffer is higher than wash buffer.

In an embodiment, the elution buffer comprises at least 6% the concentration of the 400 mM salt buffer. In an embodiment, the elution buffer comprises at least 8% the concentration of the 400 mM salt buffer. In an embodiment, the elution buffer comprises at least 10% the concentration of the 400 mM salt buffer. In an embodiment, the elution buffer comprises at least 15% the concentration of the 400 mM salt buffer. In an embodiment, the elution buffer comprises at least 20% the concentration of the 400 mM salt buffer. In an embodiment, the elution buffer comprises at least 26% the concentration of the 400 mM salt buffer.

In an embodiment, the elution is performed for about 5 CV's to about 10 CV's.

In an embodiment, the elution is performed for about 10 CV's to about 15 CV's.

In an embodiment, the elution is performed for about 15 to about 20 CV's or more. In a preferred embodiment, the elution takes place for about 19 CV's.

In an embodiment, the equilibration is performed for about 3 CV's to about 10 CV's. In a preferred embodiment, the equilibration takes place for about 5 CV's.

In an embodiment, the equilibration is performed until the equilibration buffer conductivity end point is achieved.

In an embodiment, the amount of protein loaded onto the column during loading is in the range from about 5 g/L to about 25 g/L. In an embodiment, amount of protein loaded onto the column during loading is 12.5 g/L.

In an embodiment, the washing is performed for at least about 2 CV's to about 5 CV's. In preferred embodiment, the washing is performed for about 3 CV's. In an embodiment, the washing is performed until the buffer conductivity end point is achieved.

In an embodiment, the residence time of the protein in the CHT column during equilibration washing and loading is in the range from about 2 minutes to about 6 minutes. In preferred embodiment, the residence time of the protein in the column during equilibration, washing and loading is about 4 minutes.

In an embodiment, the residence time of the protein in the column during elution has a range from about 2 minutes to about 6 minutes. In preferred embodiment, the residence time of the protein in the column during elution is about 4 minutes.

The present invention provides below examples for illustrative purpose only and invention should not be considered limiting to below examples.

The present invention provides below examples for illustrative purpose only and invention should not be considered limiting to below example:

Example 1—Evaluation of Aggregation Formation in Stored Pre-Formulation at Various pH, Concentration of Protein and Freeze Thaw Cycles All chromatographic processes were carried out using an AKTA Pure 150 system from GE Healthcare. Concentration of protein samples were determined by measuring absorbance at 280 nm using Shimadzu Spectrophotometer. MabSelect™ Sure LX resin media obtained from GE Health care, Poros HQ resin obtained from Thermo scientific and CHT XT resin media obtained from Bio-Rad. Glass columns were obtained from Merck Millipore and GE Healthcare. Turbidity was measured using Thermo scientific turbidity meter. pH was adjusted by using Mettler toledo pH meter. Protein was concentrated by using Millipore pellicon, 30 kDa, D screen RC membrane. All Chemicals were obtained from JTB or Merck Millipore and were of GMP grade.

A monoclonal antibody capable to bind to IgE expressed in Chinese Hamster Ovary (CHO) cell line is captured using Protein A (MabSelect™ Sure LX, GE Healthcare) packed in VL 11/250 column.

Eluted protein is further subjected to viral inactivation and neutralization. After neutralization, protein has been filtered by 0.2 μm filter.

Post viral inactivation and neutralization step, the eluted protein is further purified using Anion Exchange Chromatography resin (POROS 50 HQ, Thermofisher) packed in C10/20 column.

Eluted protein from Anion Exchange Chromatography (AEX) is further polished using CHT XT/Type-I resin (Bio-rad) packed in XK16/40 column.

In MMC or CHT chromatography the residence time is 4 min/3 min for all the phases. After equilibration with Na Phosphate, pH 6.8 Anion exchange (AEX) output is loaded at 12.5 mg/mL of the resin. The column is washed using 3 CV, Na Phosphate, pH 6.8. Bound protein of interest is eluted using linear gradient between 24 mM Na Phosphate and 400 mM Na Phosphate, pH 6.8.

Eluted peak of interest is analysed with SE-HPLC, CEX-HPLC for size and charge variants. The experimental design for CHT XT step is summarized in Table 1.

TABLE 1

Experimental design for CHT XT

| Step | Buffer | Residence Time (min) | Column Volume (CV) |
|---|---|---|---|
| Sanitization | 0.5N Sodium Hydroxide | 4 | 3 CV and 0.5 hr hold |
| Charge | 400 mM Na Phosphate, pH 6.8 | 4 | 3 CV |
| Equilibration | 24 mM Na Phosphate, pH 6.8 | 4 | 3 CV or conductivity end point |
| Load | AEX Eluate + 24 mM Na Phosphate, pH 6.8 | 4 | Till loading volume |
| Wash | 24 mM Na Phosphate, pH 6.8 | 4 | 2-3 CV |
| Gradient Elution | Buffer A: Water Buffer B: 400 mM Phosphate, pH 6.8 from 6% to 22% B | 4 | 19 CV |
| Strip | 400 mM Phosphate, pH 6.8 | 3 | 3 CV |
| Sanitization | 0.5N Sodium Hydroxide | 3 | 3 CV and 0.5 hr hold |
| Storage | 0.1N Sodium Hydroxide | 3 | 3 CV |

To check the impact freeze thaw of CHT XT/Type-I elute on 11MW & LMW, two different protein concentration and two different pH were studied. Total three freeze thaw cycle was conducted by keeping minimum 24 h interval between each freeze thaw cycle. Details of samples conditions are provided in below table.

TABLE 2

Impact of freeze thaw of CHT XT/Type-I elute on HMW & LMW

| Sample | pH | Conc. |
|---|---|---|
| CHT XT Elute | 7.0 | 1.43 |
| | 7.0 | 6.59 |
| | 5.8 | 1.37 |
| | 5.8 | 6.37 |

CH-T XT chromatography elute/output has pH 7.0 and protein cone. 1.43 mg/mL respectively. For freeze thaw study, p11 of CHT XT chromatography elute/output was adjusted to 5.8 using 1 M Phosphoric acid and protein concentration increased by using ultrafiltration membrane. Size related impurities were analysed by SEC-HPLC. The details of SEC-HPLC analysis of three freeze thaw cycle were provided below table.

TABLE 3

| SEC-HPLC analysis of three freeze thaw cycle | | | | | | | | |
|---|---|---|---|---|---|---|---|---|
| | % HMW by SEC-HPLC | | | | % LMW by SEC-HPLC | | | |
| FT Cycle | CHT XT Elute, pH 7.0, 1.43 mg/mL | CHT XT Elute, pH 5.8 1.37 mg/mL | CHT XT Elute, pH 7.0 6.59 mg/mL | CHT XT Elute, pH 5.8 6.37 mg/mL | CHT XT Elute, pH 7.0, 1.43 mg/mL | CHT XT Elute, pH 5.8 1.37 mg/mL | CHT XT Elute, pH 7.0 6.59 mg/mL | CHT XT Elute, pH 5.8 6.37 mg/mL |
| 0 time | 0.00 | 0.02 | 0 | 0.05 | 0 | 0 | 0 | 0 |
| FT Cycle 1 (at 7 days) | 0.16 | 0.04 | 1.16 | 0.05 | 0 | 0 | 0 | 0 |
| FT Cycle 2 (5 days after first cycle | 0.23 | 0.05 | 1.47 | 0.09 | 0 | 0 | 0 | 0 |
| FT Cycle 3 (2 days after second cycle) | 0.26 | 0.06 | 1.45 | 0.07 | 0 | 0 | 0 | 0 |

Example 2

Drug product (DP) is prepared by using preformulated CHT elute after concentrate and buffer exchange with DS formulation excipients. The final formulation comprises 20 mM of phosphate buffer, 200 mM of Arginine HCl and Poloxamer 188 at pH 6.0. Filters the bulk solution with 0.2 m PVDF filter to get the filtrated solution and fills 1 ml of filtered solution in 1 ml glass PFS which is stable for 1 month stored at 37° C. The composition of formulation is given below:

TABLE 4

| Composition of formulation | |
|---|---|
| Component | Amount |
| Omalizumab (Xolair ®) | 150 mg/mL |
| Arginine HCl | 42.1 mg/mL (200 mM) |
| Sodium phosphate monobasic monohydrate | 2.07 mg/mL (15 mM) |
| Sodium phosphate dibasic heptahydrate | 1.34 mg/mL (5 mM) |
| Poloxamer 188 | 0.4 mg/mL |

Example 3

Drug product (DP) is prepared by using preformulated CHT elute after concentrate and buffer exchange with DS formulation excipients. The final formulation comprises 20 mM of phosphate buffer, 200 mM of Lysine HCl and Poloxamer 188 at pH 6.0. Filters the bulk solution with 0.2 μm PVDF filter to get the filtrated solution and fills 1 mL of filtered solution in 1 mL glass PFS which is stable for 1 month stored at 37° C. The composition of formulation is given below:

TABLE 5

| Composition of formulation | |
|---|---|
| Component | Amount |
| Omalizumab (Xolair ®) | 150 mg/mL |
| Lysine HCl | 36.40 mg/mL (200 mM) |
| Sodium phosphate monobasic monohydrate | 2.07 mg/mL (15 mM) |
| Sodium phosphate dibasic heptahydrate | 1.34 mg/mL (5 mm) |
| Poloxamer 188 | 0.4 mg/mL |

Example 4

Drug product (DP) is prepared by using preformulated CHT elute after concentrate and buffer exchange with DS formulation excipients. The final formulation comprises 20 mM of Histidine buffer, 200 mM of Lysine HCl and Poloxamer 188 at pH 6.0. Filter the bulk solution with 0.2 μm PVDF filter to get the filtrated solution and fill 1 mL of filtered solution in 1 mL glass PFS, which is stable for 1 month stored at 37° C. The composition of formulation is given below:

TABLE 6

| Composition of formulation | |
|---|---|
| Component | Amount |
| Omalizumab (Xolair ®) | 150 mg/mL |
| Lysine HCl | 36.40 mg/mL (200 mM) |
| L - Histidine | 1.37 (11 mM) |
| L - Histidine HCl monohydrate | 2.34 (9 mM) |
| Poloxamer 188 | 0.4 mg/mL |

Example 5

DP is prepared by using preformulated CHT elute after concentrate and buffer exchange with DS formulation excipients. Omalizumab (Xolair®) lyophilized formulation comprises 202.5 mg of Omalizumab (Xolair®), 145.5 mg sucrose, 2.8 mg L-histidine hydrochloride monohydrate, 1.8 mg L-histidine and 0.5 mg polysorbate 20, pH 5.8 to 6,4 and is designed to deliver 150 mg of Omalizumab (Xolair®), in 1.2 mL after reconstitution with 1.4 mL SWFI, USP.

Filters the FI DS through a 0.2-micron filter, aliquotes (4.0 ml/vial) into 5 mL borosilicate glass vials and seal in the chamber. After lyophilization cycle completion, inspect the seal vial, label, and store at 2° C. to 8° C. The composition of formulation is given below:

TABLE 7

| Composition of formulation | |
|---|---|
| Component | Omalizumab vial |
| Omalizumab (Xolair ®) | 202.5 mg |
| Histidine | 1.8 mg |
| Histidine HCl $H_2O$ | 2.8 mg |

TABLE 7-continued

| Composition of formulation | |
|---|---|
| Component | Omalizumab vial |
| Sucrose | 145.5 mg |
| Polysorbate 20 | 0.5 mg |
| pH | 5.8 to 6.4 |

We claim:

1. A process for the preparation of a stable formulation comprising:
   (a) a pre-formulation capable to formulate in a lyophilized or a liquid formulation comprising:
      (i) an antibody of interest,
      (ii) a buffer,
      (iii) a pH;
   (b) adjusting the pH of the pre-formulation to about pH 5.0 to about 5.9;
   (c) optionally performing ultrafiltration;
   (d) storing the pre-formulation at a freezing temperature for a period of time;
   (e) performing a freeze thaw cycle of the pre-formulation;
   (f) mixing suitable excipients in the pre-formulation to formulate a final formulation;

wherein the pre-formulation comprises low aggregates or high molecular weight impurities after storing at the freezing temperature.

2. The process according to claim 1, wherein the period of time that the pre-formulation is stored is selected from the group consisting of at least 12 hours, 24 hours, 30 hours, 40 hours, 50 hours, 60 hours, 72 hours, 84 hours, 96 hours, 108 hours, 120 hours, 7 days, 10 days, 15 days, 20 days, 25 days, 30 days, 40 days, 50 days, 60 days, 3 months, 4 months, 5 months, 6 months, 7 months, 8 months, 9 months, 10 months, 11 months, and 12 months.

3. The process according to claim 1, wherein the pre-formulation freeze thaw cycle is selected from the group consisting of first cycle, second cycle, third cycle, fourth cycle, fifth cycle, sixth cycle, seventh cycle, eighth cycle, ninth cycle, and tenth cycle.

4. The process according to claim 1, wherein the pre-formulation does not comprise any sugar or sugar alcohol, wherein the sugar or sugar alcohol is selected from the group consisting of sucrose, mannitol, trehalose, raffinose, and sorbitol.

5. The process according to claim 1, wherein the pre-formulation does not comprise any amino acid, wherein the amino acid is selected from the group consisting of arginine, lysine, and glycine.

6. The process according to claim 1, wherein the adjusted pH of the pre-formulation is from about 5.5 to about 5.8.

7. The process according to claim 1, wherein the pre-formulation is obtained from chromatographic steps.

8. The process according to claim 7, wherein the chromatographic steps are selected from the group consisting of ion exchange, anion exchange, cation exchange, mixed-mode chromatography, hydrophobic exchange chromatography, and ceramic hydroxyapatite chromatography (CHT).

9. The process according to claim 7, wherein the pre-formulation-pH is identical to the pH of a buffer used for elution of the antibody of interest from a chromatographic column.

10. The process according to claim 9, wherein the pre-formulation pH is from about 6 to about 7.

11. The process according to claim 1, wherein the pre-formulation comprises a buffer, wherein the buffer is selected from the group consisting of phosphate, citrate, phosphate-citrate, histidine, and acetate, and salt thereof.

12. The process according to claim 1, wherein the pre-formulation is stored at a freezing temperature selected from the group consisting of 0° C. to −80° C., −10° C., −20° C., −30° C., −40° C., −50° C., −60° C., −70° C., or −80° C.

13. The process according to claim 12, wherein the pre-formulation is stored at a freezing temperature of 0° C. to −20° C.

14. The process according to claim 1, wherein the pre-formulation comprises low aggregates or high molecular weight impurities after the storage at a frozen temperature compared to a pre-formulation stored at pH 7.

15. The process according to claim 1, wherein the pre-formulation comprises low aggregates or high molecular weight impurities of 0.1% or less compared to a pre-formulation stored at pH 7.

16. The process according to claim 14, wherein the pre-formulation comprises low aggregates or high molecular weight impurities selected from the group consisting of about 0.09% w/v or less, 0.08% w/v or less, 0.07% w/v or less, 0.06% w/v or less, 0.05% w/v or less, 0.04% w/v or less and 0.03% w/v or less compared to the pre-formulation stored at pH 7.

17. The process according to claim 1, wherein the pre-formulation is formulated into the final formulation by mixing excipients in the pre-formulation, wherein the excipients comprise:
   (a) a buffer selected from the group consisting of phosphate, citrate, phosphate-citrate, histidine, and acetate, and salt thereof;
   (b) optionally an aggregation inhibitor selected from the group consisting of Arginine or arginine HCT, Lysine or Lysine HCT, glycine, and proline;
   (c) optionally a sugar, sugar alcohol;
   (d) a surfactant selected from the group consisting of polysorbate and poloxamer;
   (e) pH 6.0 to 7.0; and
   (f) an antibody of interest.

18. The process according to claim 17, wherein the final formulation is a liquid formulation.

19. The process according to claim 17, wherein the final formulation is a lyophilized formulation.

20. The process according to claim 1, wherein the antibody is selected from IgG1, IgG2, IgG3, IgG4, and fusion proteins thereof.

21. The process according to claim 1, wherein the antibody is IgG1 capable of binding IgE.

22. The process according to claim 1, wherein the antibody is Omalizumab or ligelizumab.

* * * * *